(12) United States Patent
Colinge et al.

(10) Patent No.: US 7,101,665 B2
(45) Date of Patent: Sep. 5, 2006

(54) METHOD FOR THE IDENTIFICATION OF GENE TRANSCRIPTS WITH IMPROVED EFFICIENCY IN THE TREATMENT OF ERRORS

(75) Inventors: Jacques Colinge, Geneva (CH); Georg Feger, Plan-les-Ouates (CH)

(73) Assignee: Applied Research Systems ARS Holdings N.V., Curacao (AN)

( * ) Notice: Subject to any disclaimer, the term of this patent is extended or adjusted under 35 U.S.C. 154(b) by 21 days.

(21) Appl. No.: 10/169,134

(22) PCT Filed: Dec. 27, 2000

(86) PCT No.: PCT/EP00/13359
§ 371 (c)(1),
(2), (4) Date: Oct. 28, 2002

(87) PCT Pub. No.: WO01/48670
PCT Pub. Date: Jul. 5, 2001

(65) Prior Publication Data
US 2003/0138794 A1    Jul. 24, 2003

(51) Int. Cl.
*C12Q 1/68* (2006.01)
(52) U.S. Cl. ............................................ 435/6; 702/20
(58) Field of Classification Search ................. 435/6; 702/19, 20
See application file for complete search history.

(56) References Cited

U.S. PATENT DOCUMENTS 5,695,937 A    12/1997    Kinzler et al.
5,970,500 A    10/1999    Sabatini et al.

FOREIGN PATENT DOCUMENTS

WO    WO 99/37816    7/1999

OTHER PUBLICATIONS

Audic et al., "The Significance of Digital Gene Expression Profiles", *Genome Research*, Oct. 1997; 7(10), pp. 986-995
Ewing et al., "Base-Calling of Automated Sequencer Traces Using *Phred*. II, Error Probabilities", *Genome Research*, Mar. 1998; 8(3), pp. 186-194.
Velculescu et al., "Serial Analysis of Gene Expression", *Science*, Oct. 1995; 270, pp. 484-487.
Velculescu, "Tantalizing Transcriptomes—SAGE and Its Use in Global Expression Analysis", *Science*, 1999, 286, pp. 1491-1942, obtained from the Internet Jun. 09, 2002 at http://www.sciencemag.org/cgl/content/full/286/5444/1491.

*Primary Examiner*—James Martinell
(74) *Attorney, Agent, or Firm*—Browdy and Neimark, PLLC

(57) ABSTRACT

A method for identification of gene transcripts comprises the steps of: generating a set of raw sequences by sequencing of biological material; isolating ditags from the set of raw sequences; isolating tags from the ditags; determining abundance of the tags; and identifying the tags, the method providing a step of reducing the amount of sequencing errors by using a statistical model for sequencing errors.

29 Claims, 18 Drawing Sheets

SAGE

Enter the new selection criteria

| | | | |
|---|---|---|---|
| UniGene | ☑ | Abundant tags <u>only</u> | no ▼ |
| RNA from EMBL | ☑ | Confidence interval | ☑ |
| Description | ☑ | Required confidence | 90 ▼ |
| One line format | ☐ | Upper ratio | 20+ ▼ |
| Mix DB output | ☐ | Lower ratio | 5 ▼ |
| Unidentified tags | ☑ | + ○ − ○ = ◉ | |
| Transition | ☐ | | |
| Show "ghost tags" | ☑ | Sequencing errors | 0.05 ▼ |

Key words ☐ [                    ]
Search the full list ☐

Tags or numbers ☐ [                    ]
Search the full list ☐

[ Display List ]   [ Update Selections ]

FIG.7

| Tag number | Ratio | Conf. | Identification and links to data bases |
|---|---|---|---|
| 49120** | 167.86 | 99.0 | (!HSJMHDRA2), HLA-DRA(HA2R_HUMAN),(!HSJMHDRH) |
| 54862* | 84.75 | 99.0 | ? |
| 4404* | 53.78 | 99.0 | ? |
| 26561* | -41.00 | 99.0 | ? |
| 38252* | 39.11 | 99.0 | ? |
| 51941** | 35.34 | 99.0 | ? |
| 56769** | -34.97 | 99.0 | ? |
| 36771* | 34.22 | 99.0 | SIM(SIM_DROME) |
| 15228* | -29.00 | 99.0 | ? |
| 94749* | 27.71 | 99.0 | ? |
| 10142** | 26.08 | 99.0 | (HB2F_HUMAN),HLA-DRB5(HB2I_HUMAN),HLA-DRB1L (Q30134), (HB2B_HUMAN),HLA-DRW12(Q29901),(HB2C-HUMAN), HLA- DRB2(Q30167), (Q19725) |
| 67843* | 26.08 | 99.0 | ? |
| 21199* | 26.08 | 99.0 | KCNJ2 OR HIRK 1(IRK2_HUMAN) |
| 16916* | -25.16 | 99.0 | ? |
| 35834* | -25.00 | 99.0 | ? |
| 48977* | 24.45 | 99.0 | ? |
| 78595* | -24.00 | 99.0 | ? |
| 100553* | -24.00 | 99.0 | ? |
| 75091* | 23.36 | 99.0 | ? |
| 48578* | 23.22 | 99.0 | ? |
| 91416** | 22.82 | 99.0 | (Hs#S1178438),HLA-DP(Q30058),(HB2O_HUMAN),HLA-DPB1 (Q30059),(HB2P_HUMAN),(!HSMHHAB),(HB2S_HUMAN), HLA-DRB1(Q19702)HLA-DRB1(Q30060) |

FIG.8

| CATGTGCATATCAT.C** | | | ratio | confidence | CIITA minus | CIITA plus |
|---|---|---|---|---|---|---|
| FULL | Show | 48933 | -10.0 | 98.0% | 10.0 | 0.0 |

| CRM1 SCHPO | UG | 3 | CRM1./CHROMOSOME REGION MAINTENANCE PROTEIN 1. |
|---|---|---|---|
| O99433 | RNA | 3 | CRM1./CRM1 PROTEIN. |
| O14980 | RNA | 2 | CRM1 PROTEIN. |

| CATGTGTGTTAAAA.G* | | | ratio | confidence | CIITA minus | CIITA plus |
|---|---|---|---|---|---|---|
| FULL | Show | 98642 | -10.0 | 98.0% | 10.0 | 0.0 |

| CATGTTAAATCCCA.T** | | | ratio | confidence | CIITA minus | CIITA plus |
|---|---|---|---|---|---|---|
| FULL | Show | 60759 | -10.0 | 98.0% | 10.0 | 0.0 |

| CD45 HUMAN | UG | 2 | PTPRC OR CD45./LEUKOCYTE COMMON ANTIGEN PRECURSOR (EC 3.1.3.48)(L-CA)(CD45 ANTIGEN) (T200). |
|---|---|---|---|
| O16614 | RNA | 3 | PTPRC./T200 LEUKOCYTE COMMON ANTIGEN (CD45, LC-A) PRECURSOR (EC 3.1.3.48)(CD45, LC-A). |

| CATGTTTAAAGCAC.T** | | | ratio | confidence | CIITA minus | CIITA plus |
|---|---|---|---|---|---|---|
| FULL | Show | 96304 | -10.0 | 98.0% | 10.0 | 0.0 |

| CATGAAACCATTCT.C* | | | ratio | confidence | CIITA minus | CIITA plus |
|---|---|---|---|---|---|---|
| FULL | Show | 76845 | -9.8 | 99.0% | 16.0 | 1.6 |

FIG. 9

| CATGGATTAAGTGA.C** | | | ratio | confidence | CIITA minus | CIITA plus |
|---|---|---|---|---|---|---|
| FULL | Show | 49135 | -7.4 | 95.0% | 12.0 | 1.6 |
| Hs#S359899 | UG | 0 | | | | |

| CATGTACAGGAAGT.T** | | | ratio | confidence | CIITA minus | CIITA plus |
|---|---|---|---|---|---|---|
| FULL | Show | 25852 | -7.4 | 95.0% | 12.0 | 1.6 |
| !AB020623 | RNA | 4 | | | | |

| CATGTACTAAAAAA.G* | | | | | ratio | confidence | CIITA minus | CIITA plus |
|---|---|---|---|---|---|---|---|---|
| FULL | Show | | 41790 | | -7.4 | 95.0% | 12.0 | 1.6 |
| NUCM BOVIN | UG | 3 | NDUFS2. | !AF050640 | RNA | 4 | | |
| NUCM HUMAN | RNA | 2 | NDUFS2. | O75306 | RNA | 2 | | |
| Pathway | Show | Ubiquinone biosynthesis | | | | | | |
| Pathway | Show | Oxidative phosphorylation | | | | | | |

| CATGTTTTATTGGA.A* | | | ratio | confidence | CIITA minus | CIITA plus |
|---|---|---|---|---|---|---|
| FULL | Show | 85660 | -7.4 | 95.0% | 12.0 | 1.6 |

FIG. 10

CATGTACTAAAAAA - Full Identification

| Numbering | | |
|---|---|---|
| | CIITA minus | CIITA plus |
| Counted | 12.00 | 1.00 |
| Adjusted | 12.00 | 1.63 |
| Estimated | (P) 12.08 | (P) 1.45 |

— 72

| Other libraries | |
|---|---|
| CIITA minus | 12.00 |
| CIITA plus | 1.63 |
| RFXAP minus | 11.23 |
| RFXAP | 21.95 |

— 73

| Neighbourhood of CATGTACTAAAAAA.G | | | |
|---|---|---|---|
| Tag | Number | CIITA minus | CIITA plus |
| CATGTGCTAAAAAA.A | 10524 | 8.00 | 1.63 |
| CATGTACTGGAAAAA | 32200 | 1.00 | 1.63 |
| CATGCACTAAAAAA | 12673 | 1.00 | 0.00 |
| CATGTACTAATAAA | 81038 | 15.00 | 8.15 |
| CATGAACTAAAAAA.A | 97106 | 81.00 | 29.33 |
| CATGTATTAAAAAA | 69831 | 1.00 | 0.00 |

— 71

70

Full identification:

QUERY CATGTACTAAAAAA.G    12    1    1.63    -7.36    7.36    0.990    0.95    41790    12

UG    Hs#S1090948, 1600, 15, ccds, F,
DE    Homo sapiens NADH-ubiquinone oxidoreductase NDUFS2 subunit mRNA, nuclear gene encoded
GENE
SPTR    P17694, NUCM_BOVIN
DE    NADH-UBIQUINONE OXIDOREDUCTASE 49 KD SUBUNIT (EC 1.6.5.3) (EC 1.6.99.3) (COMPLEX I-
GN    NDUFS2.-
KW    OXIDOREDUCTASE: NAD: UBIQUINONE: MITOCHONDRION: IRON-SULFUR: 4FE-4S.

FIG.11

| Library Sizes | | |
|---|---|---|
| | tags | different tags |
| CIITA minus | 103634 | 21303 |
| CIITA plus | 63590 | 13075 |
| CIITA | 167224 | 27215 |

| Linker Contamination | | |
|---|---|---|
| | CIITA minus | CIITA plus |
| CATGTCCCTATTAA | 3419(3.299%) | 60(0.094%) |
| CATGTCCCCGTACA | 70(0.068%) | 1518(2.387%) |

| Identified Tags | | |
|---|---|---|
| UniGene | 6643 | 24.4% |
| RNA EMBL | 4147 | 15.2% |
| All data bases | 7575 | 27.8% |

| Reliable Ratios | | | | | | |
|---|---|---|---|---|---|---|
| | 80% | 85% | 90% | 95% | 98% | 99% |
| Confidence Intervals | | | | | | |
| Ratios | 2527 | 2067 | 1107 | 787 | 423 | 300 |
| False alarms | 252.7 | 155.0 | 55.3 | 19.7 | 4.2 | 1.5 |
| Points | | | | | | |
| Ratios | 6046 | 4824 | 3303 | 1457 | 706 | 482 |
| False alarms | 597.1 | 387.6 | 183.6 | 31.9 | 5.0 | 1.5 |

| n-fold Differences at 95% Confidence | | | | | |
|---|---|---|---|---|---|
| n | 2 | 3 | 5 | 10 | 20 |
| Confidence Intervals | 682 | 548 | 281 | 79 | 24 |
| Points | 1099 | 821 | 439 | 79 | 24 |

FIG.12

| ??? no name ??? | Galactose metabolism | Oxidative phosphorylation |
|---|---|---|
| Alanine and Aspartate metabolism | | |
| | Glutamate metabolism | |
| Aminoacyl-tRNA biosynthesis | | |
| | Glutathione metabolism | |
| Aminosugars metabolism | | |
| | Glycerolipid metabolism | |
| Androgen and estrogen metabolism | | |
| Arginine and proline metabolism | Glycine, serine and threonine metabolism | Phenylalanine metabolism |
| Ascorbate and aldarate metabolism | Glycolysis Gluconeogenesis | Phenylalanine, tyrosine and tryptophan biosynthesis |
| Beta-Alanine metabolism | | |
| Bile acid biosynthesis | | Phospholipid degradation |
| Biosynthesis and degradation of glycoprotein | | Porphyrin and chlorophyl metabolism |
| Biosynthesis of flavonoids | Glyoxylate and dicarboxylate metabolism | |
| Biotin metabolism | | Propanoate metabolism |
| Butanoate metabolism | | |
| | Histidine metabolism | Prostaglandin and leukotriene metabolism |
| C21-Steroid hormone metabolism | | Purine metabolism |
| C5-Branched dibasic acid metabolism | Inositol phosphate metabolism | |
| Carbon fixation | Lysine biosynthesis | |
| | Lysine degradation | |
| | Metabolism of xenobiotics | |
| Citrate cycle (TCA cycle) | Methane metabolism | Pyrimidine metabolism |
| | Methionine metabolism | |
| Cyanoamino acid metabolism | | |
| | Nicotinate and nicotinamide metabolism | |
| Cysteine metabolism | Nitrogen metabolism | |
| D-Arginine and D-ornithine metabolism | | |
| | | Pyruvate metabolism |
| D-Glutamine and D-glutamate metabolism | Nucleotide sugars metabolism | |
| Fatty acid biosynthesis (path 1) | One carbon pool by folate | |
| Fatty acid biosynthesis (path 2) | Pantothenate and CoA biosynthesis | Reductive carboxylate cycle (CO₂ fixation) |
| Fatty acid metabolism | | |

FIG.14

| Tag number | Ratio | Conf. | Identification and links to data bases |
|---|---|---|---|
| 49120 | 167.86 | 100.0 | (!HSJMHDRA2), HLA-DRA(HA2R_HUMAN), (!HSJMHDRH) |
| 54862 | 84.75 | 100.0 | ? |
| 4404 | 53.78 | 100.0 | ? |
| 26561 | -41.00 | 100.0 | ? |
| 38252 | 39.11 | 100.0 | ? |
| 51941 | 35.34 | 100.0 | ? |
| 56769 | -34.97 | 100.0 | ? |
| 36771 | 34.22 | 100.0 | SIM(SIM_DROME) |
| 15228 | -29.00 | 100.0 | ? |
| 94749 | 27.71 | 100.0 | ? |
| 10142 | 26.08 | 100.0 | (HB2F_HUMAN), HLA-DRB5(HB2I_HUMAN), HLA-DRB1L (Q30134), (HB2B_HUMAN), HLA-DRW12(Q29901), (HB2C_HUMAN), HLA-DRB2(Q30167), (O19725) |
| 67843 | 26.08 | 100.0 | ? |
| 21199 | 26.08 | 100.0 | KCNJ2 OR HIRK1(IRK2_HUMAN) |
| 16916 | -25.16 | 100.0 | ? |
| 35834 | -25.00 | 100.0 | ? |
| 48977 | 24.45 | 100.0 | ? |
| 78595 | -24.00 | 100.0 | ? |
| 100553 | -24.00 | 100.0 | ? |
| 75091 | 23.36 | 100.0 | ? |
| 48578 | 23.22 | 100.0 | ? |
| 91416 | 22.82 | 100.0 | (Hs#S1178438), HLA-DP(Q30058), (HB2Q_HUMAN), HLA-DPB1(Q30059), (HB2P_HUMAN), (!HSMHHAB), (HB2S_HUMAN), HLA-DPB1(O19702), HLA-DPB1(Q30060) |
| 44994 | 22.52 | 100.0 | ? |
| 6241 | -22.00 | 100.0 | ? |
| 83059 | -20.00 | 100.0 | HSPE1(CH10_HUMAN) |
| 4986 | 19.56 | 100.0 | ? |
| 71876 | 19.56 | 100.0 | ? |
| 66644 | -19.00 | 100.0 | CYC1(CY1_HUMAN) |
| 64278 | -17.00 | 100.0 | ? |
| 96535 | -15.34 | 100.0 | ? |
| 56080 | -15.00 | 100.0 | ? |
| 19256 | -15.00 | 100.0 | ? |
| 98484 | 14.67 | 100.0 | ? |
| 7552 | 14.67 | 100.0 | ? |
| 50638 | 14.67 | 100.0 | ARL3(ARL3_HUMAN), HLA-DPA1 OR HLASB (HA2Q_HUMAN), (!HSSBA1) |
| 63337 | -14.00 | 99.9 | (Hs#S1264020), (Hs#S389247), (!AF043250) |

FIG. 18

SEQUENCE LISTING

<160> NUMBER OF SEQ ID NOS: 20

<210> SEQ ID NO 1
<211> LENGTH: 13
<212> TYPE: DNA
<213> ORGANISM: Artificial
<220> FEATURE:
<223> OTHER INFORMATION: Synthetic

```
<400> SEQUENCE: 1
catgcaaatt att                                                          13

<210> SEQ ID NO 2
<211> LENGTH: 15
<212> TYPE: DNA
<213> ORGANISM: Artificial
<220> FEATURE:
<223> OTHER INFORMATION: Synthetic

<400> SEQUENCE: 2
catgaccctc ttcca                                                        15

<210> SEQ ID NO 3
<211> LENGTH: 15
<212> TYPE: DNA
<213> ORGANISM: Artificial
<220> FEATURE:
<223> OTHER INFORMATION: Synthetic

<400> SEQUENCE: 3
catgtgcata tcatc                                                        15

<210> SEQ ID NO 4
<211> LENGTH: 15
<212> TYPE: DNA
<213> ORGANISM: Artificial
<220> FEATURE:
<223> OTHER INFORMATION: Synthetic

<400> SEQUENCE: 4
catgtgtgtt aaaag                                                        15

<210> SEQ ID NO 5
<211> LENGTH: 15
<212> TYPE: DNA
<213> ORGANISM: Artificial
<220> FEATURE:
<223> OTHER INFORMATION: Synthetic

<400> SEQUENCE: 5
catgttaaat cccat                                                        15

<210> SEQ ID NO 6
<211> LENGTH: 15
<212> TYPE: DNA
<213> ORGANISM: Artificial
<220> FEATURE:
<223> OTHER INFORMATION: Synthetic

<400> SEQUENCE: 6
catgtttaaa gcact                                                        15

<210> SEQ ID NO 7
<211> LENGTH: 15
<212> TYPE: DNA
<213> ORGANISM: Artificial
<220> FEATURE:
<223> OTHER INFORMATION: Synthetic

<400> SEQUENCE: 7
catgaaacca ttctc                                                        15

<210> SEQ ID NO 8
<211> LENGTH: 15
```

```
<212> TYPE: DNA
<213> ORGANISM: Artificial
<220> FEATURE:
<223> OTHER INFORMATION: Synthetic

<400> SEQUENCE: 8
catggattaa gtgac                                                    15

<210> SEQ ID NO 9
<211> LENGTH: 15
<212> TYPE: DNA
<213> ORGANISM: Artificial
<220> FEATURE:
<223> OTHER INFORMATION: Synthetic

<400> SEQUENCE: 9
catgtacagg aagtt                                                    15

<210> SEQ ID NO 10
<211> LENGTH: 15
<212> TYPE: DNA
<213> ORGANISM: Artificial
<220> FEATURE:
<223> OTHER INFORMATION: Synthetic

<400> SEQUENCE: 10
catgtactaa aaaag                                                    15

<210> SEQ ID NO 11
<211> LENGTH: 15
<212> TYPE: DNA
<213> ORGANISM: Artificial
<220> FEATURE:
<223> OTHER INFORMATION: Synthetic

<400> SEQUENCE: 11
catgttttat tggaa                                                    15

<210> SEQ ID NO 12
<211> LENGTH: 14
<212> TYPE: DNA
<213> ORGANISM: Artificial
<220> FEATURE:
<223> OTHER INFORMATION: Synthetic

<400> SEQUENCE: 12
catgtactaa aaaa                                                     14

<210> SEQ ID NO 13
<211> LENGTH: 15
<212> TYPE: DNA
<213> ORGANISM: Artificial
<220> FEATURE:
<223> OTHER INFORMATION: Synthetic

<400> SEQUENCE: 13
catgtgctaa aaaaa                                                    15

<210> SEQ ID NO 14
<211> LENGTH: 15
<212> TYPE: DNA
<213> ORGANISM: Artificial
<220> FEATURE:
<223> OTHER INFORMATION: Synthetic

<400> SEQUENCE: 14
```
catgtactgg aaaaa                                              15

<210> SEQ ID NO 15
<211> LENGTH: 14
<212> TYPE: DNA
<213> ORGANISM: Artificial
<220> FEATURE:
<223> OTHER INFORMATION: Synthetic

<400> SEQUENCE: 15
catgcactaa aaaa                                               14

<210> SEQ ID NO 16
<211> LENGTH: 14
<212> TYPE: DNA
<213> ORGANISM: Artificial
<220> FEATURE:
<223> OTHER INFORMATION: Synthetic

<400> SEQUENCE: 16
catgtactaa taaa                                               14

<210> SEQ ID NO 17
<211> LENGTH: 15
<212> TYPE: DNA
<213> ORGANISM: Artificial
<220> FEATURE:
<223> OTHER INFORMATION: Synthetic

<400> SEQUENCE: 17
catgaactaa aaaaa                                              15

<210> SEQ ID NO 18
<211> LENGTH: 14
<212> TYPE: DNA
<213> ORGANISM: Artificial
<220> FEATURE:
<223> OTHER INFORMATION: Synthetic

<400> SEQUENCE: 18
catgtattaa aaaa                                               14

<210> SEQ ID NO 19
<211> LENGTH: 14
<212> TYPE: DNA
<213> ORGANISM: Artificial
<220> FEATURE:
<223> OTHER INFORMATION: Synthetic

<400> SEQUENCE: 19
catgtcccta ttaa                                               14

<210> SEQ ID NO 20
<211> LENGTH: 14
<212> TYPE: DNA
<213> ORGANISM: Artificial
<220> FEATURE:
<223> OTHER INFORMATION: Synthetic

<400> SEQUENCE: 20
catgtccccg taca                                               14

METHOD FOR THE IDENTIFICATION OF GENE TRANSCRIPTS WITH IMPROVED EFFICIENCY IN THE TREATMENT OF ERRORS

This invention relates to a method for identification of gene transcripts such as RNAs or their corresponding cDNAs with an improved efficiency in the treatment of errors. The method can be applied to collect information from several cell types, for example with reference to DGE (Differential Gene Expression) studies.

In particular, a method is disclosed which applies a SAGE method for sequencing data. The results thus obtained are then used in a comparative way in order to provide a gene identification.

According to U.S. Pat. No. 5,695,937 assigned to the Johns Hopkins University (see also Velculescu et al., Serial Analysis of Gene Expression, Science, 270: 484–487, 1995 and Velculescu Tantalizing Transcriptomes, SAGE and its use in global gene expression analysis, Science 286: 1491–1492, 1999), tags are obtained and after that dimerized before determination of the nucleotide sequence thereof. The dimerized tags are known with the term of "ditags". In more detail, U.S. Pat. No. 5,695,937 describes a method for serial analysis of gene expression, which comprises the steps of: 1) Producing cDNA oligonucleotides; 2) Isolating a first defined nucleotide sequence tag from a first cDNA oligonucleotide and a second defined nucleotide sequence tag from a second cDNA oligonucleotide; 3) Linking the first tag to a first oligonucleotide linker, wherein the first oligonucleotide linker comprises a first sequence for hybridization of an amplification primer and linking the second tag to a second oligonucleotide linker, wherein the second oligonucleotide linker comprises a second sequence for hybridization of an amplification primer; and 4) Determining the nucleotide sequence of the tag(s), wherein the tag(s) correspond to an expressed gene.

The main disadvantage associated with the procedure set forth above lies in the elevated percentage of error associated thereto.

Differential genetic expression methods are for example known from Kal et al., Dynamics of gene expression revealed by comparison of serial analysis of gene expression transcript profile from yeast grown on two different carbon sources, Mol. Biol. of the cell, 10: 1859–1872, 1999 and from WO 95/20681, in the name of Incyte Pharmaceuticals, Inc. A method is therein described, which compares the gene transcript image analysis from two or more biological specimens and identifies one or more genes which are differentially expressed between the two specimens.

A first object of the method according to the present invention is that of providing a method which greatly reduces the error rate of the tags obtained for example through a method like the SAGE method, by estimating the error rate and consequently rejecting dangerous tags.

A second object of the present invention is that of providing an easy way of consulting the identified tags, by use of an improved graphical interface. Access to the full set of information (full identification story and abundance in other libraries) concerning a tag is given.

The present invention solves the aforementioned problems by providing a method for identification of gene transcripts comprising the steps of:

a) generating at least a first set of raw sequences by sequencing at least a first type of biological material;
b) isolating first ditags from said at least first set of raw sequences;
c) isolating first tags from said isolated at least first ditags;
d) determining abundance of said first tags; and
e) identifying said first tags, further comprising a step of
f) reducing the amount of sequencing errors by using a statistical model for sequencing errors to be applied to said isolated first tags.

Advantageous embodiments of the invention will be disclosed in the attached dependent claims.

The term "biological material" will relate to material directly or indirectly derived from an eucariotic or procariotic cell, including at least part of the ribonucleic acids anyhow present in such cell.

The terms "raw sequence" and "raw data" will relate to sequences of nucleotides derived from the biological material through techniques known in the art.

With the term "tag" a partial, defined sequence of transcripts corresponding to a gene segment is intended. Therefore, a tag is a marker for genes which are expressed in a cell, a tissue, or an extract for example. A tag is generally a short nucleotide sequence of 9 to 10 base-pairs, which contains an information content to uniquely identify a transcript, provided it is isolated from a defined position within the transcript. Tags of different measures can also be obtained.

The main advantage of the method according the present invention is that of greatly reducing the problem of sequencing errors. This goal is reached by applying a statistical model for sequencing errors.

A second advantage of the method is that it provides a measure of the correctness of the identification by also allowing the user to confirm this identification through use of more than one database. For example, an EST database can be firstly used and then the positive matches can be confirmed through a search in a protein database like SWISS-PROT.

A further advantage lies in the way the results are presented. The method provides not only a text form which is richer than other interfaces for, similar data (e.g. SAGE data) in terms of information about identified tags, but also an improved graphical interface which allows an easy interpretation of the results and an easy access to e.g. the KEGG pathway.

Other advantages and features will be readily apparent to the person skilled in the art upon reading of the following detailed description.

Reference will be made to preferred non-limiting exemplary embodiments of the present invention with reference to the annexed figures, wherein.

Figure 13:
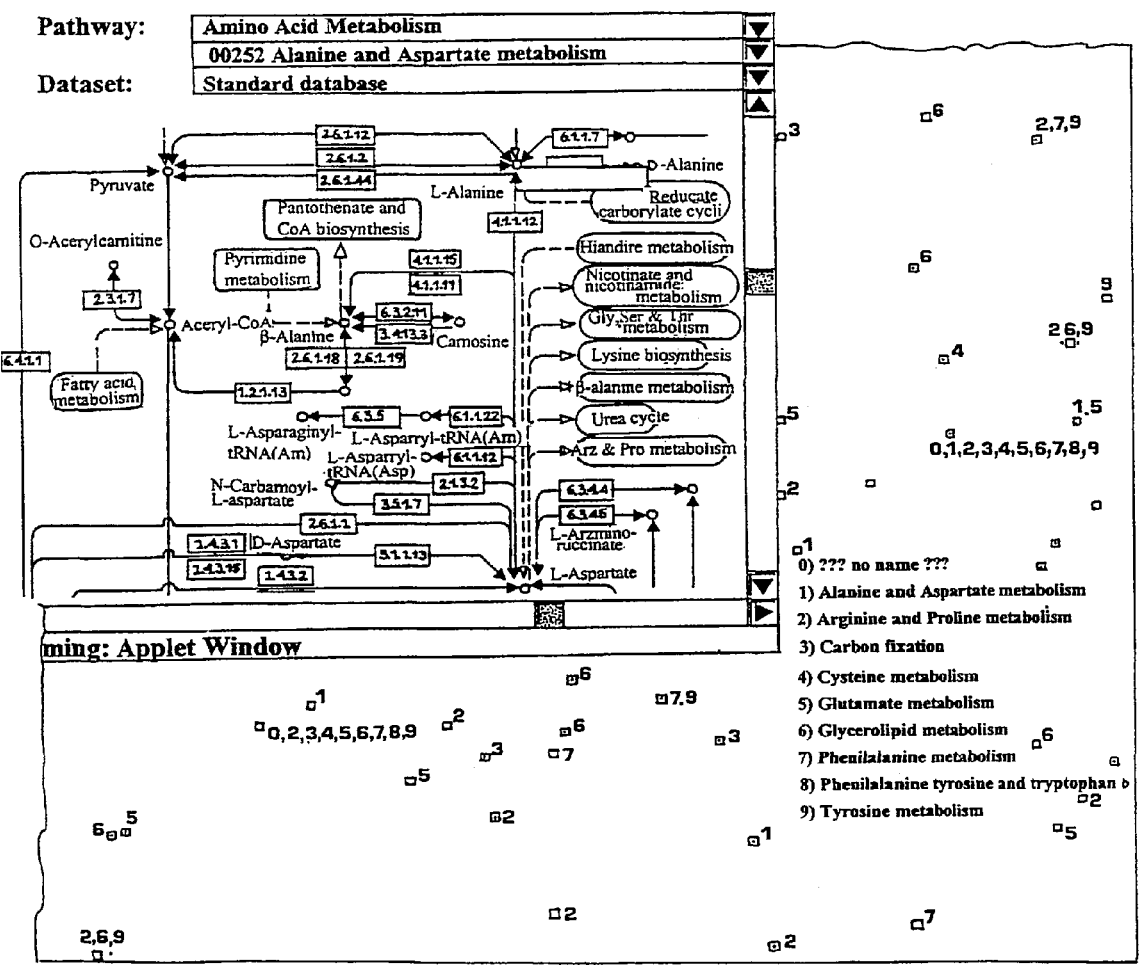

FIGS. 7 to 12 show visualization displays of the identified data (the nucleotide sequences displayed in FIGS. 9–12 are as follows: the first sequence in FIG. 9 is SEQ ID NO: 3; the second sequence in FIG. 9 is SEQ ID NO: 4; the third sequence in FIG. 9 is SEQ ID NO: 5; the fourth sequence in FIG. 9 is SEQ ID NO: 6; and the fifth sequence in FIG. 9 is SEQ ID NO: 7; the first sequence in FIG. 10 is SEQ ID NO: 8; the second sequence in FIG. 10 is SEQ ID NO: 9; the third sequence in FIG. 10 is SEQ ID NO: 10; and the fourth sequence in FIG. 10 is SEQ ID NO: 11; the first sequence in FIG. 11 is SEQ ID NO: 10; the second sequence in FIG. 11 is SEQ ID NO: 12; the third sequence in FIG. 11 is SEQ ID NO: 13; the fourth sequence in FIG. 11 is SEQ ID NO: 14; the fifth sequence in FIG. 11 is SEQ ID NO: 15; the sixth sequence in FIG. 11 is SEQ ID NO: 16; the seventh sequence in FIG. 11 is SEQ ID NO: 17; and the eighth sequence in FIG. 11 is SEQ ID NO: 18; and the first sequence in FIG. 12 is SEQ ID NO: 19; and the second sequence in FIG. 12 is SEQ ID NO: 20.);

FIGS. 13 and 14 show different operational modes for providing a global and/or particular view of the data; and FIGS. 15 to 18 show results relating to a specific example processed according to the present invention.

A computer program which implements the present invention, and which was originally presented as part of the specification as originally filed, is contained in a computer program listing appendix contained on a compact disc submitted to the U.S. Patent and Trademark Office on Dec. 23, 2004. The compact disc contains the following files:

annex1.txt, created on Feb. 9, 2001, and 5,898 bytes in size
annex2.txt, created on Feb. 9, 2001, and 12,954 bytes in size
annex3.txt, created on Feb. 9, 2001, and 7,394 bytes in size
annex4.txt, created on Feb. 9, 2001, and 5,243 bytes in size
annex5.txt, created on Feb. 9, 2001, and 19,149 bytes in size
annex6.txt, created on Feb. 9, 2001, and 6,444 bytes in size
annex7.txt, created on Feb. 9, 2001, and 28,128 bytes in size
annex8.txt, created on Feb. 22, 2001, and 23,818 bytes in size The material contained on the compact disc is incorporated by reference herein in its entirety.

Figure 1:
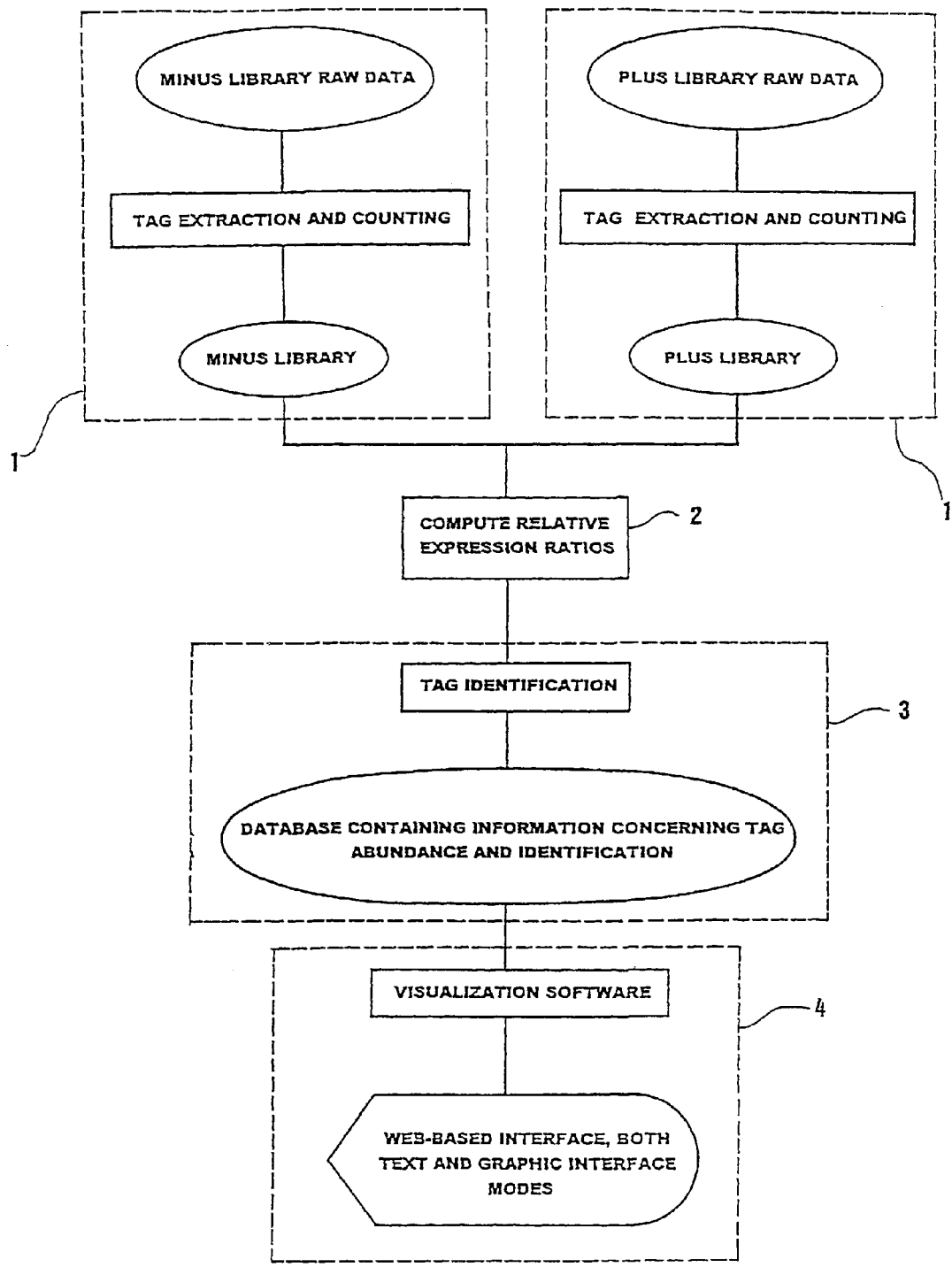
FIG. 1 shows a flow chart representing a general overview of the method according to the present invention.

With reference now to FIG. 1, a general overview of the method according to the present invention is shown. The method comprises four steps.

In a first step 1 raw data are processed starting from biological material. In particular, starting from the biological material of a cell, RNA is isolated, its corresponding cDNA constructed and tags and subsequently ditags are chained together, therefore following the SAGE method.

In the preferred embodiment, this step 1 is applied to two distinct libraries of raw data, each library of raw data relating to a particular cell type. For example, the "minus" library of FIG. 1 can relate to a neutral cell type while the "plus" library of FIG. 1 can relate to an ill cell type. In this way a particular biological state, disease or condition which is correlated to the relative abundance of gene transcripts in a cell or population of cells can be determined. Of course this step could also be applied to a single library of data, the relative abundance being in this case computed between transcripts of the same cell.

Subsequently to this, tags are extracted from the ditags and counted. This generates a file containing the list of each detected tag with the corresponding abundance 20, i.e. the number of times the tags is present within the library.

In a second step 2 comparison between the data of the minus and of the plus library is effected. In this step the tags detected in each cell type are organized, their abundance is compared (e.g. by computing a ratio therebetween) and useful information about up-regulation and down-regulation is produced as a result.

In a third step 3 tag identification is performed. It has to be noted that the tags are a kind of "fingerprint" for expressed mRNA sequences which, in turn, correspond to expressed genes. Therefore, in this step the genes that correspond to the detected tags are identified. The identification step requires a comparison between each detected tag and a database of nucleotide sequences, such as Unigene and/or EMBL. A further aim of this step is also that of providing references with other databases such as SWISS-PROT (a protein database), KEGG, PROSITE, Pir and Pfam. Background material on these databases can be found for example in: Stoesser et al., The EMBL Nucleotide Sequence Database, Nucleic Acids Res., 27:18–24, 1999; Ogata et al., KEGG: Kyoto Encyclopedia of Genes and Genomes, Nucleic Acids Res., 27:29–34, 1999; Bateman et al., Pfam 3.1: 1313 Multiple Alignments and Profile HMMs Match the Majority of Protein, Nucleic Acids Res., 27:260–262, 1999; Barker et al., The PIR-International Protein Sequence Database, Nucleic Acids Res., 27:39–43, 1999; Hoffmann et al., The SWISS-PROT Protein Sequence Data Bank and its Supplement TrEMBK in 1999, Nucleic Acids Res., 27:49–54, 1999, Bairoch et al., The SWISS-PROT Protein Sequence Data Bank and its Supplement TrEMBK in 1999, Nucleic Acids Res., 27:49–54, 1999, Welle et al., Inventory of High-Abundance mRNAs in skeletal muscle of normal men, Gen. Res., 5:506–513, 1999, Yermolaeva et al., Data management and analysis for gene expression arrays, Nat. Gen., 20: 19–23, 1998, Chen et al., Ratio-based decision and the quantitative analysis of cDNA Micro-array images, J. Of Biomedical Optics, 2: 364, 1997, Schuler et al., A gene map of the human genome, Science 274: 540–546, 1996.

Therefore, after performing step 3, a database containing information about the identified tags, their abundance, their corresponding gene description is obtained, with links to different protein and nucleotide databases.

In a fourth step 4 the results are displayed. A visualization software provides both a text and a graphical mode for the presentation of the resulting data on a web-based user interface. This allows the user to access all the desired information in an easy way.

In the following, the method will be explained in more detail with reference to FIGS. 2 to 14.

Figure 2:
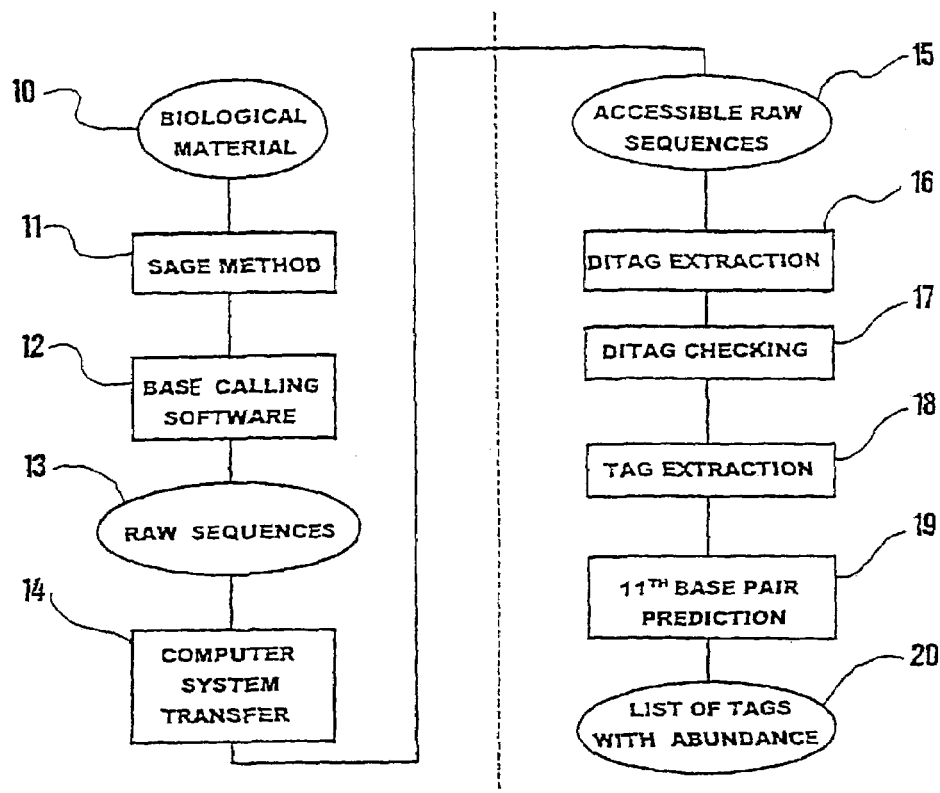
FIG. 2 shows a flow chart representing the step of extracting tags from biological material.

FIG. 2 shows the various substeps contained in step 1 of FIG. 1.

A first step 11 is that of applying a method like the SAGE method to the biological material 10.

In a subsequent step 12, a base-calling method performed through a base-calling software, for example an ABI® sequence analysis software or a PHRED® base-calling software, sequences the chains of tags obtained with the SAGE method, by producing raw sequences 13. These raw sequences are a series of bases one after the other, which still need to be properly identified. For a detailed description of the cited softwares, reference can be made to the following papers: ABI PRISM. DNA Sequencing Analysis Software, User's Manual, PE Applied Biosystems, 1996, Ewing et al., Base-Calling of Automated Sequencer Traces Using PHRED®, Gen. Res., 8: 175–185, 1998, Connell et al., Automated DNA Sequence Analysis, Biotechniques, 5: 342–248.

In a step 14, the raw sequences 13 are transferred to a second computer system and transformed in raw sequences 15 of a type which can be used by the second computer system, for example through formatting operations.

A further procedure 16 operates by isolating ditags from each raw sequence 15 by cleavage when encountering for example the subsequence CATG. As an example, procedures operating in accordance with type IIS enzymes like BsmFI, MmeI and FokI can be used.

After having performed isolation of the ditags, the method according to the present invention advantageously performs a procedure 17, which checks the isolated (extracted) ditags for removing inappropriate or wrong material. In particular a ditag is rejected on the basis of the following four rules:

Rule based on the particular base-calling software used: The ABI® sequence analysis software puts and "N" each time a bad quality signal is detected. Therefore, each time an N is encountered, the corresponding ditag is rejected. The PHRED® base-calling software gives an estimation of the confidence level of each base-pair. Therefore, each time a ditag has a confidence level which is lower than a predeteremined threshold, the ditag is rejected;

Rule based on the length of the ditags: if the ditag is too small, i.e. smaller than 20 base-pairs it is rejected, because it does not contain two entire tags;

Rule based on the length of the ditags: If the ditag is too large, i.e. larger than 24 base-pairs it is rejected, because the cleaving BsmFI enzyme, which is normally used in a SAGE method, should not produce such large tags; or If the ditag occurs twice it is rejected, because there is a risk of over PCR amplification. In fact, if it is assumed that the tags are randomly paired to form ditags, then the probability to have twice the same ditag is very low.

Once this selection has been done, a procedure 18 extracts tags from the isolated and selected ditags. Each 20 base-pairs long ditag contains two 10 base-pairs long tags: one starting from its 5' end and the other, complementary reverse coded, from its 3' end. It has to be noted that a 20 base-pair long ditag could also contain a first 11 base-pair long tag and a second 9 base-pair long tag. Nevertheless, this situation is neglected in the preferred embodiment because, when for example adopting the BsmFI enzyme, it is very rare to have tags of this size.

For what concerns cases of polymorphism (i.e. different sequences for the same gene) one exemplary approach which could be taken into consideration is that of choosing one determined sequence (and therefore one determined tag) to represent that gene, if the gene is known. If the gene is not known and it is polymorphic, there is of course the possibility of detecting two different tags which in fact relate to the same gene.

The extracted tags are also counted. In a preferred embodiment of the present invention, a procedure 19 tries to predict an extra base-pair for each different tag during the counting operation. This prediction is for example possible when adopting a SAGE method by using a BsmFI enzyme. This enzyme generally gives tags with a length of more than 10 base-pairs.

The prediction step 19 comprises the following substeps:

It is assumed that the different occurrences of each tag are equally distributed at 5' ends and 3' ends of the ditag. This means that the possible extra base-pair located in the middle of a ditag can be symmetrically assigned to the tag;

Each time a ditag is encountered, if its length is at least a predetermined number of base-pairs (22 base-pairs in the present embodiment), then one extra base-pair is assigned to each of its two tags. Having in mind the above assumption, the extra-base pair assignment is straightforward;

Once all the tags have been extracted from the ditags, each of them is successively considered, in order to decide whether there is a reasonable possibility to predict an extra base pair. First of all, it is imposed that the tag must be at least as much abundant as a certain threshold, in order for the statistics of the 11th base-pair to have a meaning. For those tags which satisfy such a criterion, the most dominant 11th base-pair is chosen and it is imposed that such most dominant 11th base-pair for that tag must represent at least a certain percentage of the number of occurrences of the tag. If this is the case, the extra base-pair is considered as acceptable.

According to a preferred embodiment of the present invention the prediction step 19 is performed applying an improved method for di-tags processing that no longer relies on fixed thresholds on tags and 11th base abundance. Instead, hypothesis testing techniques are used for estimating the relevance of the predicted 11th bases. It is the possible to choose a minimum relevance, like 95% for instance, and only accept the corresponding predictions.

The procedure is the following: assuming that each base has the same probability to be sequenced (null hypothesis), the method can be performed applying the following algorithm.

Algorithm

Let $c(t)$ be a counter associated with a tag t. Let $A(t)$, $C(t)$, $G(t)$, $T(t)$ be counters associated with each possible extra base of the tag t. Let s be a sequence and $R(s)$ the operation to take the complementary reverse of s (read s in reverse order and exchange letters 'A' with 'T' and 'C' with 'G'.

a) For each di-tag d of length k;

Take 10 bases at each end of d in order to obtain the two tags t1 and t2 (t1=d[1 . . . 10] and t2=R(d[k−10 . . . 1]));

Increment the counters c(t1) and c(t2);

If k>=22, extract one extra base for each tag: b1=d[11] and b2=R(d[k−11]);

Increment the respective base counters, for example if b1='A' then increment A(t1), etc. The same for b2;

b) Select the extra bases that have a degree of relevance greater than a given threshold, for example of 95% or 99% according with data in the following Table I:

TABLE I

Number of 11th base prediction for human normal white matter SAGE library

| Relevance | Number of predictions | Average count | Median count |
|---|---|---|---|
| 95.0% | 1700 (432) | 28.8 (8.5) | 25 (7) |
| 99.0% | 1268 (488) | 35.7 (10.7) | 20 (13) |
| 99.99% | 780 | 51.4 | 22 |

In this table statistics about tag abundance for each relevance degree are given both as the average and median counts. Statistics for a specific relevance degree only are in parentheses; and c) For each different tag which has at least one of its extra base counter different from 0, test whether each of the selected extra bases is relevant (is possible that more than one extra base is relevant).

The step c) can be performed comparing the observed frequencies with the hypothetical situation of equiprobability. In particular:

Let D be the counter of the extra base to test and let Q the sum of the others counter and N=D+Q. If N is not a multiple of 4 then add 1, 2 or 3 to N in order to have N a multiple of 4 and:

if D>N/4 then the tested extra base can be considered relevant;

if D<=N/4 then the tested extra base can be considered non-relevant.

The relevance for each predicted extra-base is computed by using a contingency table and applying chi-squared statistics with one degree of freedom or by computing Fisher's exact test, as disclosed in: "Everitt BS: The analysis of contingency tables. London: Chapman and Hall, 1977".

Chi-squared statistics allow for estimating the significance of the departure from the null hypothesis.

A possible contingency table is the following Table II:

TABLE II

Contingency table

| | Extra base to test | Others | Total |
|---|---|---|---|
| Observed count | D | Q | N = D + Q |
| Null hypothesis | N/4 | 3N/4 | N |

In the above disclosed algorithm are only considered di-tags of length at least 22-bases. 21-bases long di-tags are not considered because the distribution of di-tags lengths shows that there are enough 22-bases long di-tags, and because 21-bases long di-tags would generate too many wrong 11th base counts, hence making the application of the hypothesis testing more difficult. This is shown in the following Table III:

TABLE III

Di-tag length distribution for human normal white matter SAGE library

| Di-tag length | Number detected | Percentage |
|---|---|---|
| 20 | 233 | 0.5% |
| 21 | 2524 | 5.3% |
| 22 | 25502 | 53.3% |
| 23 | 17052 | 35.7% |
| 24 | 2151 | 4.5% |
| 25 | 129 | 0.3% |
| 26 | 191 | 0.4% |

Checking of consistence of this possible extra base-pair will be explained later in this description.

The tag extraction step up to now described can be repeated for one or more sets of raw data and terminate with respective generations of lists of tags containing also information on their abundance 20. Having in mind what already set forth in FIG. 1, the preferred embodiment of the present invention provides two distinct tag extraction steps with reference to two respective distinct raw data collections.

Figure 3:
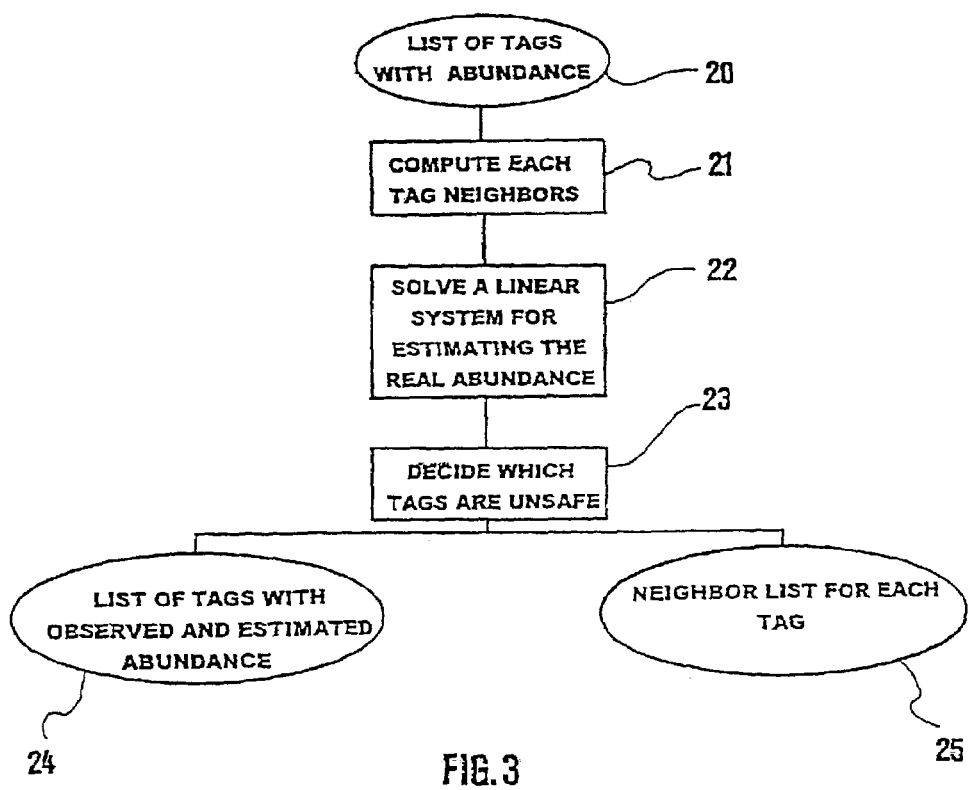
FIG. 3 shows a flow chart representing the step of reducing sequencing errors.

Subsequent FIG. 3 shows a step of reduction of the sequencing errors, to be preferably performed between steps 1 and 2 of FIG. 1.

The aim of this step is that of eliminating or rejecting tags which have not been sequenced correctly, in order to avoid generation of wrong information. In the preferred embodiment this step is performed two times, one for each library.

As a matter of fact, each tag that is not sequenced correctly generates a wrong piece of information. Either it generates a non-existing tag, which is called a ghost tag, or it increases the number of occurrences of another tag, which is really present. In the first case, the ghost tag can be either identified, so that the user wrongly thinks the corresponding gene is present, or it is not identified, so that the user might wrongly imagine there is a potential finding for a new gene. In the second case, the expression level of the really present tag is modified incorrectly.

A first approach for reducing the influence of sequencing errors could be that of using ABI® sequence analysis software for base-calling and simply rejecting tags/ditags that have at least one unidentified base-pair.

A similar approach could be that of using PHRED® base-calling software or any base-calling method which assigns a confidence level to each predicted base-pair, and rejecting tags/ditags that have at least one base-pair with a confidence level below a given threshold.

However, according to the present invention, a better throughput has been obtained by defining a sequencing error statistical model and by advantageously combining this method with the base-calling methods or software like ABI® sequence analysis software and PHRED® base-calling software.

In a first embodiment the application of the statistical model will be performed without or after use of a base-calling method. In a second embodiment, even the application of statistical model per se will be mixed with a base-calling software like PHRED®. In particular, this last combination has been made possible by converting a confidence level into a probability that a base-pair is not correct, and therefore by treating the confidence level of a base-calling software like PHRED® as a particular statistical model.

The two embodiments shall be disclosed in detail after a definition of statistical model and after the presentation of an example.

By statistical model, a function of the type

F: ST×ST→[0, 1]

is intended, where ST is the set of every possible tag to be considered, with $$\sum_{b \in S_T} F(a, b) = 1, \forall\ a \in S_T.$$

The function F is intended to modelize the probability that a given tag a, i.e. the corresponding cDNA sequence, can be sequenced as b. This probability is given by the function F(a, b). A simple example of a possible function F will follow hereinafter.

Example of a Possible Function F

Since the average probability that a base-pair is not correctly sequenced, i.e. the average sequencing error rate, is generally estimated around 1%, the probability of having one error in a 10 base-pairs tag (BsmFI enzyme) can be estimated as follows:

$$1 - P(\text{no error}) = 1 - C_{10}^0 (0.01)^0 (0.99)^{10} \cong 0.096 (= 9.6\%)$$

The influence of multiple errors will be here neglected, and only cases where one error is possible for each tag shall be considered. The possible errors to be considered shall be:

base exchange: one base-pair is sequenced as another (e.g. A for G or T for A, etc.);

insertion: one random base-pair is inserted between two base-pairs or at the beginning of the tag. This means that one base-pair is lost at the end of the tag;

suppression: one base-pair is deleted and a random base-pair is added at the end of the tag.

For every tag a ∈ST, the value of F(a,b), ∀ b∈ $S_T$, shall be defined as follows:

i) b = a $$F(a, a) = C_{10}^0 (0.01)^0 (0.99)^{10} = (0.99)^{10} -$$

ii) b ≠ a

Let $V_a \subset S_T$ be the set of every "neighbour" tag $b \in S_T$ which can be "reached" from a by one of the three types of errors above considered.

Let $N_a = \# V_a$, i.e. the number of elements in the set $V_a$.
Then $F(a,b)$ is defined as follows:

$$F(a, b) = \frac{1 - (0.99)^{10}}{N_a}, \forall b \in V_a$$

$$F(a,b) = 0, \forall b \notin V_a$$

A possible choice for $S_T$ is the set of observed tags.

Now the two distinct embodiments above introduced for estimating the real abundance of each tag will be discussed in detail.

First Embodiment

According to this embodiment, preferably in a first step a base-calling software like ABI® sequence analysis softaware or PHRED® base-calling software will be firstly applied to the ditags or to the tags, and only after that the subsequent procedure shall be followed.

Let $y \in \Re^n$ be the list (seen as a vector) of every corrected tag abundance. After having assumed an average sequencing error rate and after having assumed a statistical model for the representation of sequencing errors, a linear system can be written, of the type $Ax=y$, $x \in \Re^n$, $A \in \Re^{n \times n}$, where x is an estimation of the real abundance, not influenced by sequencing errors, to be found as a solution of the linear system.

Let $a_{ij}$ be a matrix element of A, being i its row index and j its column index.

The line j of the matrix A represents the contribution of every tag (before sequencing errors) to what has been observed (after sequencing errors). Matrix A is filled by applying the following procedure:

For each $tag_i$, $1 \leq i \leq n$ (procedure 21 of FIG. 3), $a_{ii} = F(tag_i, tag_i)$ $a_{ki} = F(tag_i, tag_k), tag_k \in V_{tagi}$.

With $tag_i$ a tag has been intended, which abundance is stored at position i in vectors y and x.

It has to be noted that, when the function F of the previous example is applied, it follows that $$F(a, a) \gg \sum_b F(a, b), b \in V_a$$

and therefore that A is sparse and diagonal dominant. This means that $AX=y$ (procedure 22 of FIG. 3) can be efficiently solved by Lanczos-type methods like BiCGSTAB for instance.

After solution of the system, a decision procedure 23 could be performed in order to reject each tag for which the difference between the counted abundance and the above calculated estimated abundance is bigger than a given threshold.

As an alternative, this last procedure could be performed by the visualization interface, and the estimated abundance value could be simply added to the file where the tags and their counted abundance are stored, in order to give to the user this information as well.

Second Embodiment

In this embodiment, the confidence level provided by PHRED® (or by similar software producing a confidence level) is transformed into a probability that the base-pair is not correct, with the formula Confidence level $=-10 \log_{10}$ (probability).

After this, the probabilities thus obtained can be directly used in the statistical model definition in order to define a different function F and best fit the real data. Prior to the application of such statistical model, the above mentioned base-calling software can be advantageously applied.

In an embodiment where the raw sequences are not trimmed as usual but, instead, a SAGE specific quality check procedure is applied, it could be not clear whether the usual 1% average sequencing error rate is correct.

In order to solve this problem, an advantageous procedure will be now described, by which the average probability that a base pair is not correct can be calculated.

It is assumed to make use of an enzyme that generates tags of a length n, with n large enough in order for tags of length m<n not to provide less information concerning the number of expressed genes in a given cell type. This means to assume that n-m extra base-pairs available in the longer tags are useless for identifying different mRNA sequences, as soon as the first m base-pairs are given.

It is also assumed, as a sequencing error model, that there is an average sequencing error rate q and that each base-pair has the same probability to be wrong. Moreover, it is assumed that the probability that a wrongly sequenced tag is equal to another sequenced tag is negligible.

Let N be the total number of sequenced tags and $k_n$, $k_m$ be the numbers of different detected tags by successively considering tags of n and m base-pairs.

By defining d to be the correct number of different tags, the following system is obtained:

$$\begin{cases} k_n = d - (1 - (1-q)^n)N \\ k_m = d - (1 - (1-q)^m)N \end{cases}$$

This system is easily solved by using a Gröbner basis and the solution not only gives d but also q, providing an estimation of the sequencing error rate. This method has been applied with success by the inventors for n=19 (MmeI enzyme) and m=14, 15, 16, 17. The resulting approximation was 0.003<q<0.006 (therefore between 0.3% and 0.6%), the exact value of q depending on the library.

The step of reducing sequencing errors produces two separate lists in the preferred embodiment up to now described. One of those lists, indicated by numeral 24 in FIG. 3, contains the observed tags with their estimated abundance, and the other, indicated by numeral 25, contains the neighbour list for each tag.

Figure 4A:
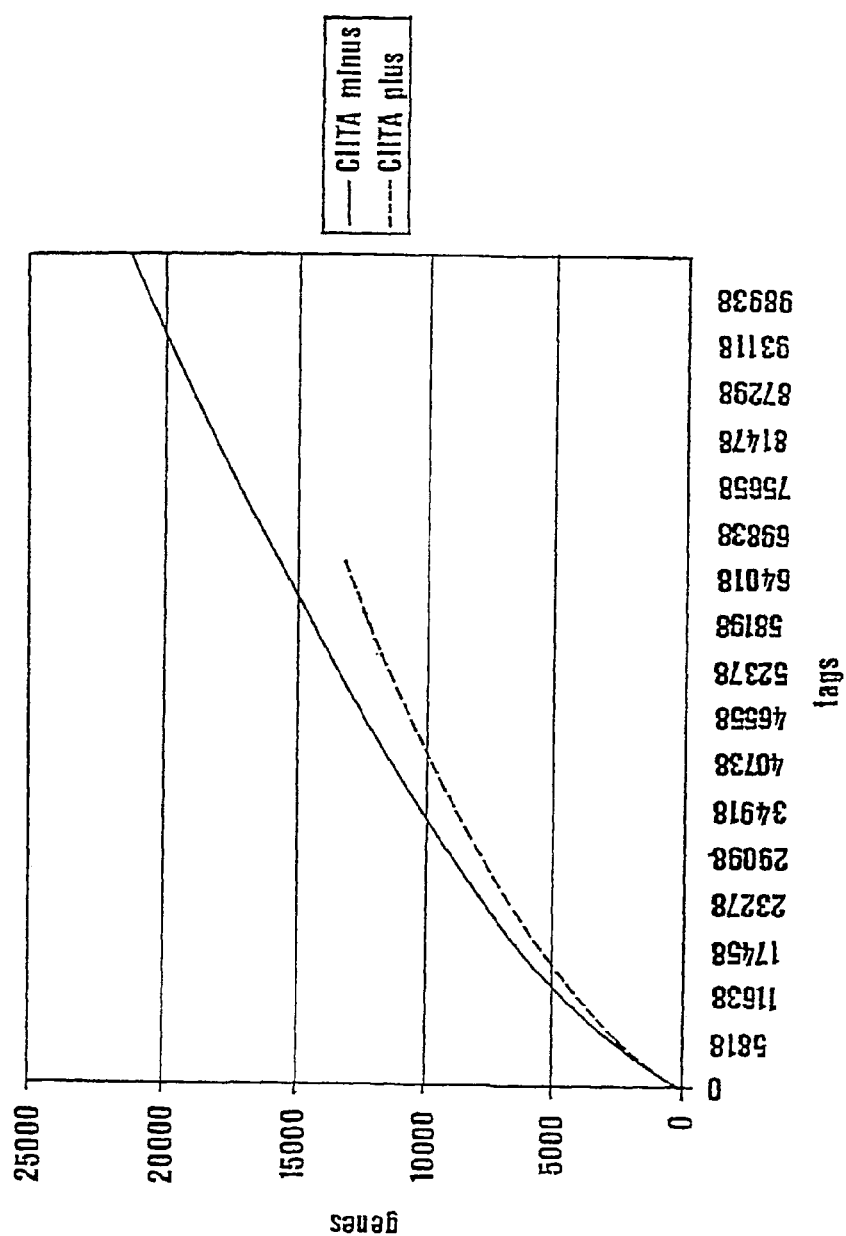
FIGS. 4A and 4B show graphs referring to the number of detected tags.

To avoid the problem of "oversequencing" the biological material, the method according to the present invention can be used to monitor how many different tags have been detected with respect to how many tags have been sequenced. In this connection, FIG. 4A shows an example of such a curve, plotted in a Cartesian system, where on the x-axis the number of sequenced tags and on the y-axis the number of detected tags are shown for each library. According to this curve the operator is provided with an objective information for deciding when to stop sequencing.

A possible interesting application is, having assumed that the sequencing error contribution has been made negligible, to estimate the number of expressed genes in a given cell type. The curve can be computed by maintaining a kind of chronology, since the tags are essentially sequenced in a random order, by assigning a random "date" to each sequenced tag.

Figure 4B:
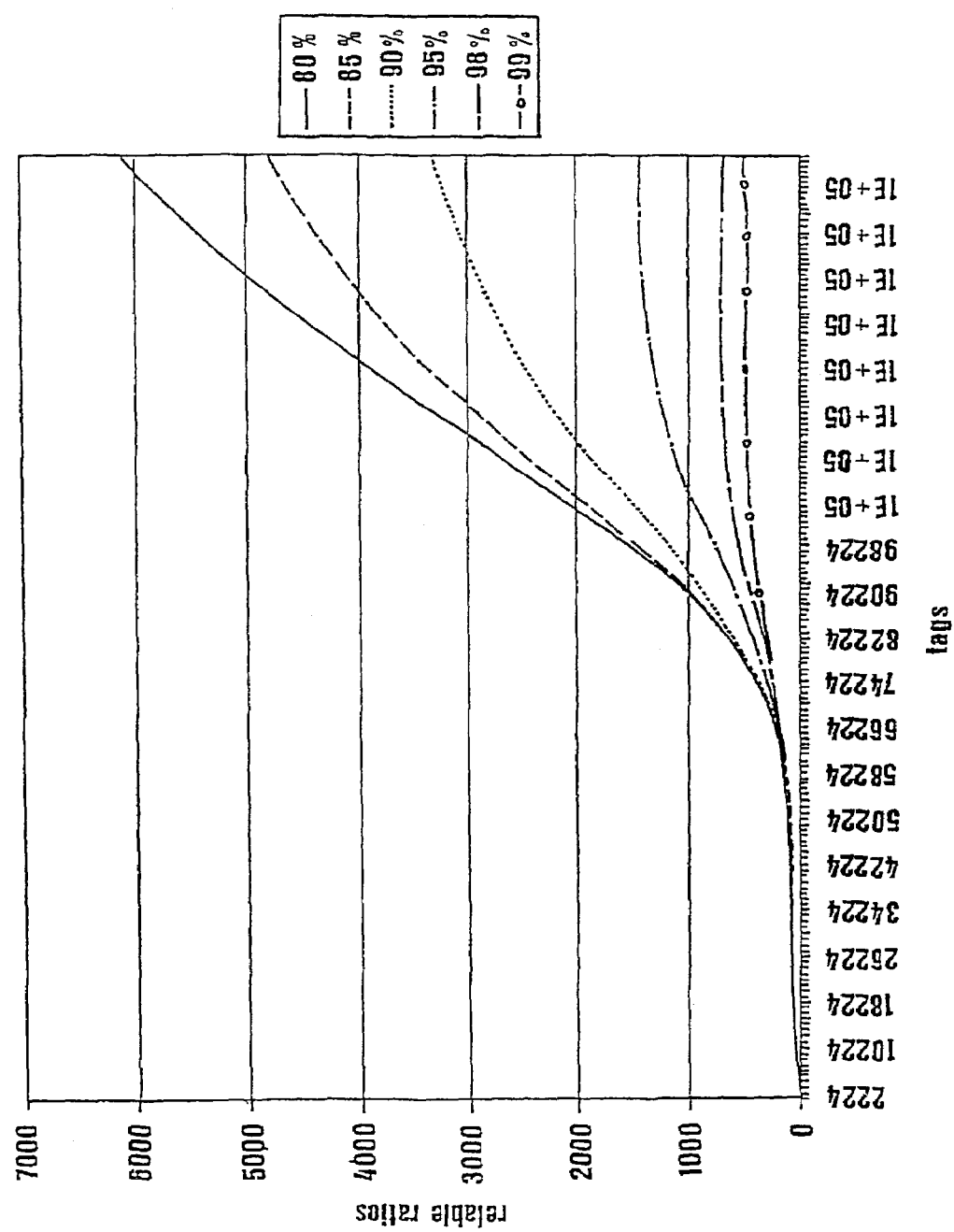

FIG. 4B shows a curve where on the x-axis the number of sequenced tags is shown and on the y-axis the reliable ratios are shown, i.e. the ratios between the sequenced and the detected tags.

As in the case of the tag number curve, a chronology is obtained, either real or random, and therefore for each "date" a pair of libraries is obtained, each containing a certain number of different tags with their abundance.

Consequently, for each "date", a method presented in Claverie et al. can be applied, for several confidence levels, estimating the number of reliable ratios. The results can be plotted as curves and provide and efficient way (more information than the tag number curves) to monitor a project progress. The application of such method will be discussed at a further stage of the present description.

Figure 5A:
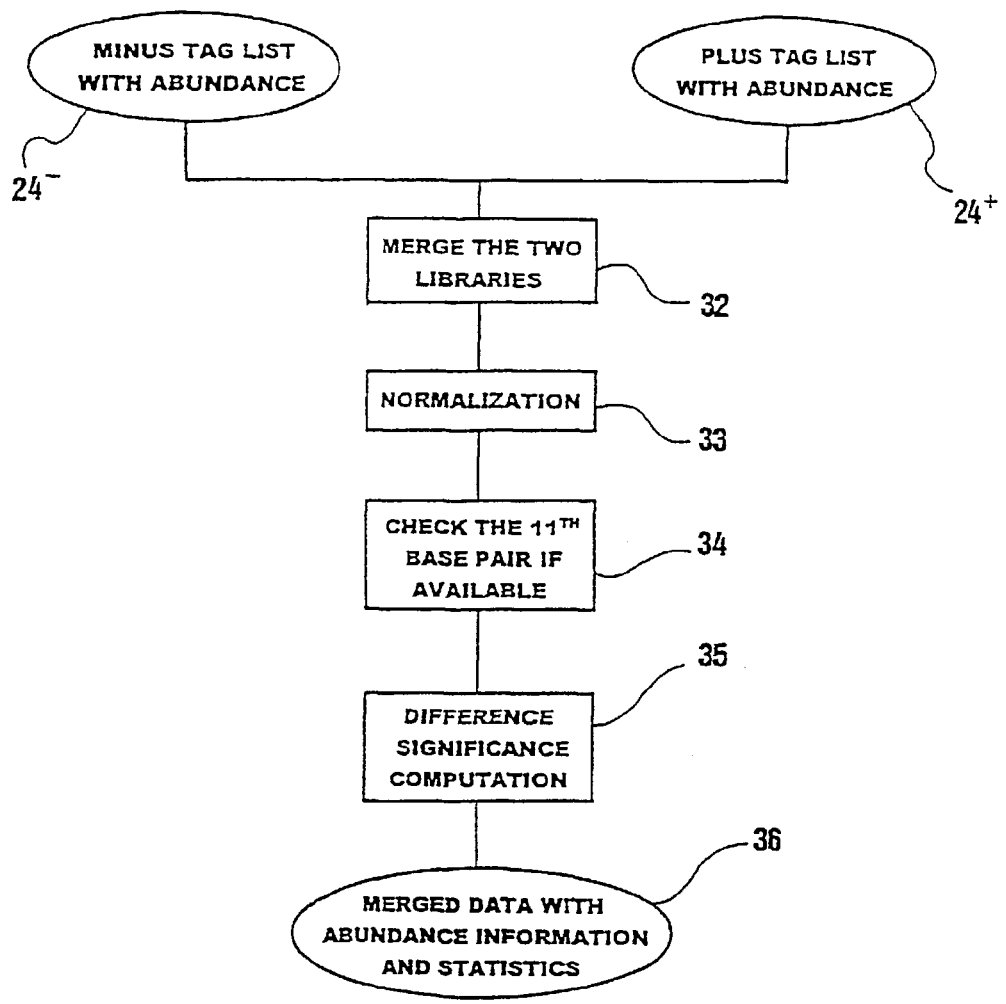
FIG. 5 shows a flow chart representing the step of comparing two sets of tags.
Figure 5B:
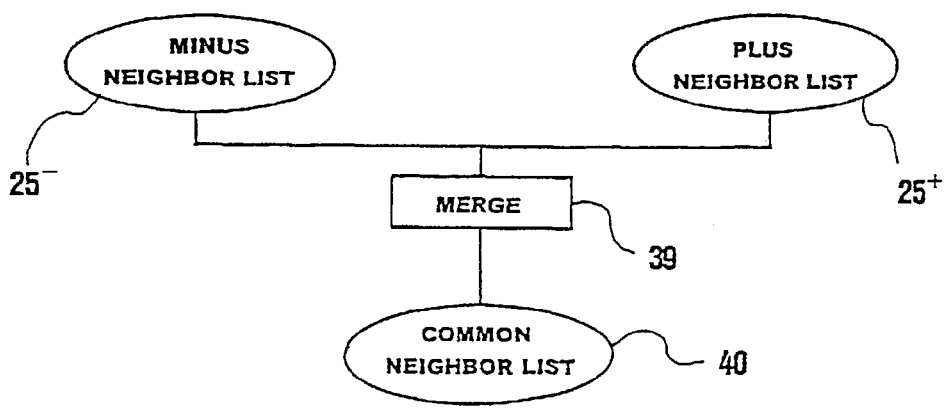

FIGS. 5A and 5B show in detail step 2 of FIG. 1.

In FIG. 5A, the two lists of tags, i.e. the minus library $24^-$ and the plus library $24^+$, both generated by the preceding step of reducing sequencing errors, are merged together by a software procedure 32 which generates a new list also containing the abundance information for the two cell types.

The number of occurrences of each tag is also normalized, because each library contains a different number of sequenced tags. This operation is performed by a software procedure 33 and can be done by simply applying a factor to the abundance of the tags in e.g. the second library. This factor is obtained by dividing the total number of tags sequenced for the first library by the total number of tags sequenced for the second library.

A further normalization mode could be that of making use of housekeeping genes.

Next, a procedure 34 checks each tag for the consistence of the 11th base-pair prediction previously made, by applying the following rules:

if the tag is present only in one library, then the 11th base-pair prediction is conserved;

if the tag is present in both libraries and the 11th base-pair prediction coincides, then it is conserved;

if the tag is present in both libraries and the 11th base-pair prediction does not coincide, then the abundance of the tag in each library is considered. In particular, if the tag has been counted more times than a given threshold in the first library and less times than another threshold in the second library, the 11th base-pair prediction is conserved only for the tag coming from the first library.

In any other situation the 11th base-pair prediction is rejected.

After this checking operation, a procedure 35 computes statistics about the significance of the observed differences between the two cell types. For example, if a tag Ta has an abundance equal to 1 in the first library and an abundance equal to 2 in the second library, and a tag Tb has an abundance equal to 100 in the first library and equal to 200 in the second library, it is easily understood that the second tag Tb has a bigger difference significance than the first tag Ta.

In order to estimate the probability that an observed difference is correct, the procedure 35 applies an improved method of that described in Claverie et al., *The Significance of Digital Gene Expression Profiles*, Gen. Res., 7:986–995, 1997. These statistical results are stored in a new file with the list of tags and their abundance, as shown by the number 36 in the figure.

By using a statistics similar to that of Claverie et al, a new set of curves is computed, as shown in FIG. 4B. These curves give the number of tags which have at least a certain confidence level, with respect to the total number of sequenced tags and therefore allow a better planning of the use of the sequencers.

With reference now to FIG. 5B, the neighbourhood information coming from the respective minus list 25− and plus list 25+ (see also FIG. 3), is also merged together in step 39, in order to form a new common neighbour list 40 that will be used by the subsequent visualization interface, as later described.

Figure 6:
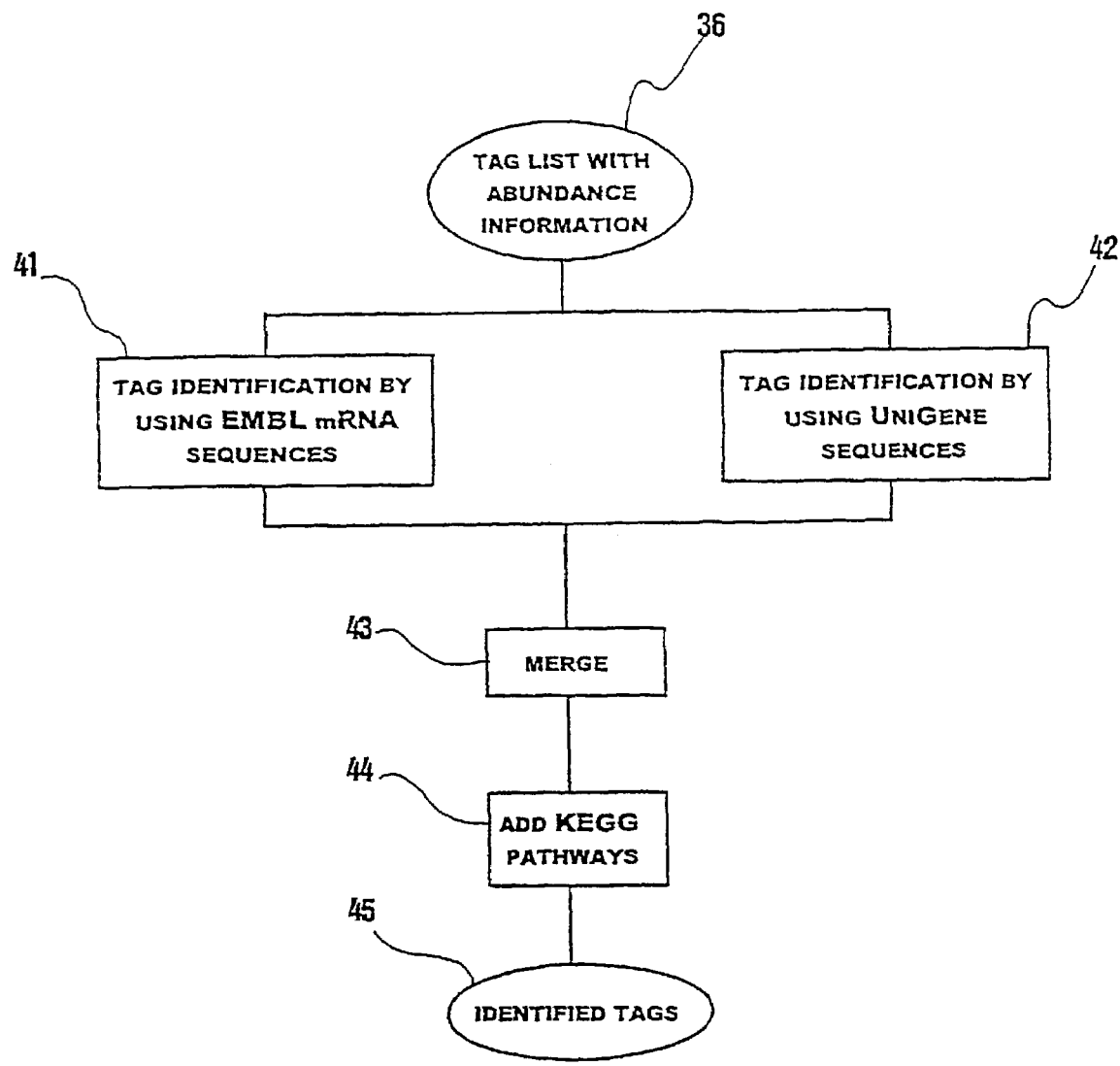
FIG. 6 shows a flow chart representing the step of identifying the tags.

FIG. 6 shows in detail the tag identification step 3 of FIG. 1.

The tag identification step is accomplished by extracting SAGE tags from each entry of a nucleotide sequence database (for example EMBL with reference to mRNA entries only, EGAD or Unigene) and by comparing the tags extracted from the database with the tags to identify.

Several are the advantageous modes by which this procedure is effected.

First of all, a tentative is made to provide an identification of the tags in terms of genes, i.e. in terms of a SWISS-PROT entry, by making use of a SWISS-PROT database. This is done by building a new database which includes all those EMBL entries that are pointed by at least one SWISS-PROT entry, in order to firstly compare the tags with this kind of entries. In this way the maximum number of links to SWISS-PROT from EMBL is obtained.

Another advantageous embodiment consists in assigning a score to each identification. Independently from the kind of database, this score-assigning procedure is useful in order to reduce the redundant and/or partial information contained in the databases. For example, it is very common for such databases that several entries concern the same gene, giving partial sequences and both expressed and genomic material. Another reason for not taking the identifications for granted is that SAGE tags start at the last NIaIII restriction site (CATG) before the poly-A. In a database it is not clear if the given sequence goes up to the poly-A. This means that if a database does not include information like "complete coding sequence" or "poly-A at . . . ", there is a risk that the database entry tag is not the same as the real SAGE tag.

The score assigning procedure depends on the particular database which is used.

FIG. 6 shows the procedures used in order to identify the tags present in the list 36 (see also FIG. 5), by using a Unigene database (step 42) and a EMBL database (step 41).

With reference to the Unigene database, tags are extracted from the database (both 3' end and 5' end tags) in order to build a new database. The SAGE tags are then matched against this new database, searching for occurrences. A typical entry of the new database looks like the following:

| | |
|---|---|
| UG | Hs#S4384, 2532 |
| DE | Alcohol dehydrogenase 2 (class I), beta polypeptide |
| GENE | ADH2 |
| TAG | CATGCAAATTATT (SEQ ID NO:1), CATGACCCTCTTCCA (SEQ ID NO:2) |

-continued

```
SPTR    P00325, ADHB_HUMAN

DE      ALCOHOL DEHYDROGENASE BETA CHAIN
        (EC 1.1.1.1)

GN      ADH2

KW      OXIDOREDUCTASE; ZINC; NAD; MULTIGENE FAMILY;
        ACETYLATION; POLYMORPHISM; 3D-STRUCTURE

SUBLOC  CYTOPLASMIC

PROSIT  PROSITE; PS00059; ADH_ZINC; 1.\

PFAM    PFAM; PF00107; adh_zinc; 1.\
```

A score is assigned to each identification, computed according to the following rules:

the score is given an initial value of 0;

1 is added to the value if the Unigene sequence length is larger than a given threshold. This length is the second item on the UG line of the entry (2532 in the example above). This criterion is used to measure the probability for the Unigene sequence to include the real SAGE tag;

1 is added to the value if the 11th predicted base-pair of the tag is available and matches with the Unigene entry tag;

1 is added to the value if the Unigene description (DE line) includes the word "ccds" indicating with this a complete coding sequence (this is not the case of the example above);

1 is added to the value if the tag has matched with the 3' end Unigene tag and the Unigene description contains "3'", or if the tag has matched with the 5' end Unigene tag and the Unigene description contains "5'";

1 is subtracted from the value if the Unigene sequence length is smaller than a given threshold;

1 is subtracted from the value if the Unigene description includes the word "pcds" indicating a partial coding sequence (this is not the case of the example above);

1 is subtracted from the value if the tag has matched with the 3' end Unigene tag and the Unigene description contains "5'" or if the tag has matched with the 5' end Unigene tag and the Unigene description contains "3'"; and 1 is subtracted from the value if the SWISS-PROT description, if available, contains the word "FRAGMENT".

The commercially available database EGAD could be used similarly.

With reference now to the EMBL and SWISS-PROT databases, a SAGE new database is built and used for matching SAGE tags, as for Unigene. Also in this case an identification score is computed, according to the following rules:

the score is given an initial value of 0;

1 is added to the value if the EMBL sequence length is larger than a given threshold;

1 is added to the value if the 11th predicted base-pair of the tag is available and matches with the EMBL entry tag;

1 is added to the value if the EMBL description (DE line) includes the word "ccds";

1 is added to the value if the EMBL entry feature contains an indication that the sequence runs to the poly-A;

1 is subtracted from the value if the EMBL sequence length is smaller than a given threshold;

1 is subtracted from the value if the EMBL description includes the word "pcds";

1 is subtracted from the value if the 11th predicted base-pair of the tag is available but does not match with the EMBL entry tag; and 1 is subtracted from the value if the SWISS-PROT description, if available, contains the word "FRAGMENT".

In each case, it is simple to ascertain that the identification score goes from −4 to +4.

A subsequent procedure 43 merges the results of the previous identification steps in a single new file and a procedure 44 looks if the identified tags, or their corresponding genes, are member of a biological pathway by using their SWISS-PROT accession number and the KEGG database. This new information is added to the file 45.

The identification procedure so far described does not exploit the information stored in EST databases, neither it exploits the genomic (DNA) material of EMBL. The inventors have tested with positive results the approach of looking for the tags in an EST database (e.g. dbEST) and, for each EST found, apply a Blast (see Altschul et al., *Basic Local Alignment Search Tool*, J. Mol. Biol., 215: 403–410, 1990) or a Fasta (see Pearson, *Improved Tools for Biological Sequences Comparison*, Proc. Natl. Acad. Sci. USA, 85:2444–2448, 1988) against a protein database (e.g. SWISS-PROT). In this case, in order to avoid the inconvenient of a generation of false positives when treating small tags (14 or 15 base pairs, the initial CATG being included in the tag), a MmeI restriction enzyme was advantageously used, which produces 19 base pairs tags.

Once the tag identification step has been completed, the operator can access all the information by an user interface which comprises both a text web interface and a graphic web interface.

The Text Web Interface is designed to give access to the information produced after the tag identification and is shown in detail in next FIGS. 7 to 12.

FIG. 7 shows a first input form the user can fill in order to set several parameters and then to select the subset of data he wants to consider. The richness of the parameters the user can select is possible thanks to the various steps of the present invention up to now described.

The result of this selection can be displayed in several different modes through several different web pages that will be shown in subsequent FIGS. 8 to 12.

FIG. 8 shows a web page on which the information for each tag is summarized in a single line with four fields. These fields represent:

The Tag Number. This number is unique for each tag. The item is an hyperlink (underlined) which brings the user to the full set of information about the tag (Tag Full Story). The asterisks following the number are an indication whether the tag is safe or not with reference to the sequencing errors;

The Ratio, which is computed by considering the abundance, after normalization, of each tag in both the minus and the plus library. Let n be the abundance in the minus type and let m be the abundance in the plus type, then:

| | |
|---|---|
| Ratio = m/n | if m > n |
| Ratio = −n/m | otherwise |

The Confidence Statistics (previously described in this description); and

A short description (Identification and links to databases) complemented by hyperlinks to different databases (underlined items).

FIG. 9 shows a web page on which the information for each tag is more detailed. In particular, the abundance of the tag in each library (see numerals 60 and 61) is shown and more than one identification for the same tag is displayed. These identifications are sorted with respect to the identification score 62 (from higher to lower) and marked with a label 63 which indicates the database of origin.

The hyperlink labelled FULL brings again the user to the Tag Full Story, while the button labelled "Show" corresponds to the graphic display.

FIG. 10 shows a standard mode without description, where the descriptions of the tags are eliminated to make place to a possible second column of identifications.

FIG. 11 shows a tag full story, where every possible information about the selected tag is displayed. It includes every detail 70 of its identification, neighbourhood information 71, abundance 72 and abundance 73 in other libraries. Every abundance is normalized with respect to the current comparison so that each data can be easily compared.

FIG. 12 shows a page in which the user has access to statistical information concerning the current comparison. This page also contains hyperlinks to the already mentioned plots of FIGS. 4A and 4B.

FIGS. 13 and 14 show the graphic web interface. The identification of the tags comprises an assignment of a number to each identified tag, which identifies the tag in a unique manner.

Starting from this number, a position on the screen is calculated for each tag, so that each tag is represented by a different pixel on the graphic interface, independently from the used database. This particular approach improves the "Virtual Chip" concept developed by Larson, 1999.

Herebelow, the method for human cell types is described.

The human being has about 100.000 genes. In order to display the tags on a square graphic display, a number which is a square is selected, for example 102.400, which equals to 320 times 320. Further to this, numbers between 0 and 102.399 are assigned to the tags as follows:

at the beginning every number from 0 to 102.399 is set as available; and each time a new tag is detected, an available number is randomly chosen among the remaining available numbers.

The Graphic Interface is intended to provide a global view of the data. It has two operational modes, shown in FIGS. 13 and 14.

FIG. 13 shows the principal mode.

In this mode, the point associated to a tag depends on the unique tag number. The coordinates of this point, in a 320 by 3.20 matrix, is given by:

line (y coordinate), which equals to the result of the integer division of the tag number by 320; and column (x coordinate), which equals to the remainder of the above integer division.

A colour of the point is also chosen, which depends on the expression ratio. As the cursor passes over the points, this mode also gives extra information, like numerical value of the ratio, gene name for identified tags and tag number.

By clicking on a point, the user puts the selected tag on the top of the text display. From this moment, complete information concerning the tag is accessible.

FIG. 14 shows a further mode of representing the data. Only identified tags are shown, possibly grouped according to a specific property, e.g. with respect to KEGG pathways.

FIGS. 15 to 18 show an example of the method according to the present invention, called CIITA, where the promoter of a deficient gene has been restored. This gene controls immunology genes, HLA.

By the way, already discussed FIG. 12 shows the statistics of this experiment, referred to the library sizes, to the linker contamination, to the identified tags to the reliable ratios and to the confidence values. The minus cell is the cell with no promoter, while the plus cell is the cell with the restored promoter, the HLA cells being expressed in the plus cell.

Figure 15:
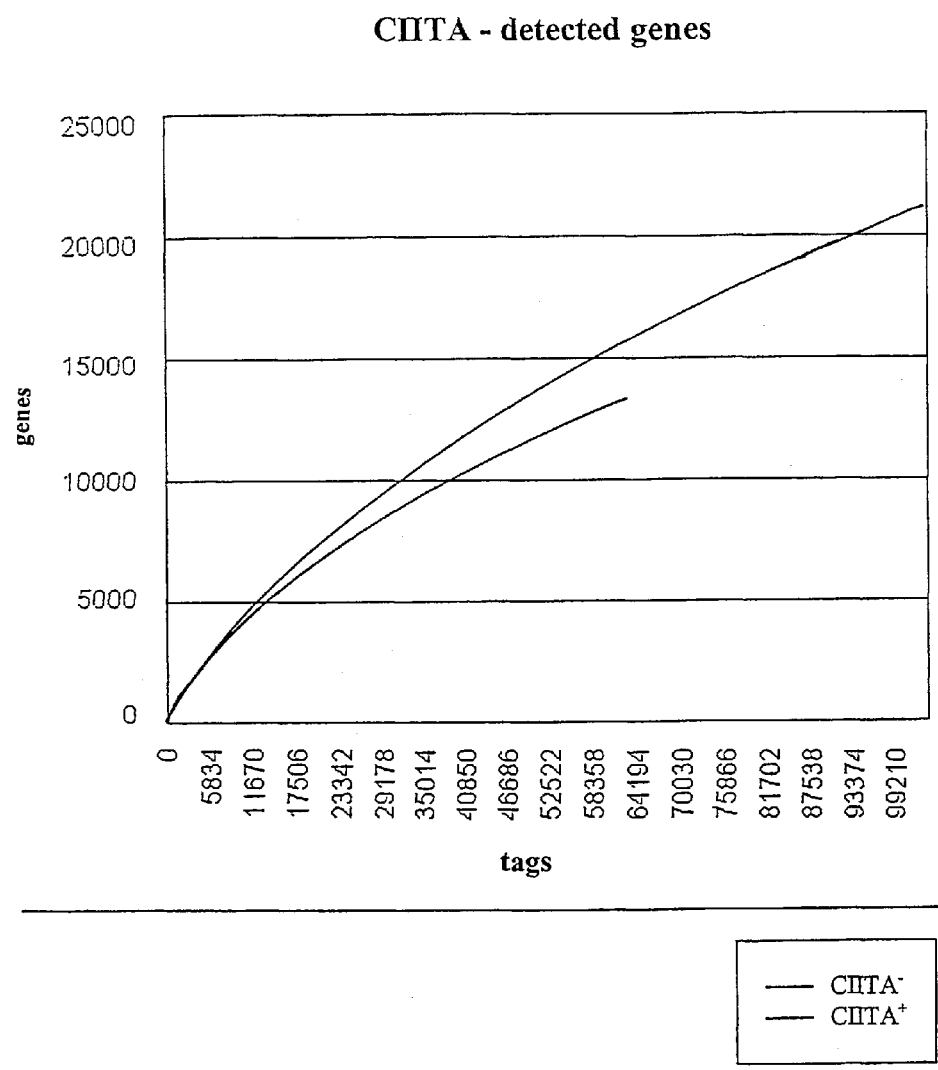

FIG. 15 shows for this example a graph of the type already discussed with reference to FIG. 4A.

Figure 16:
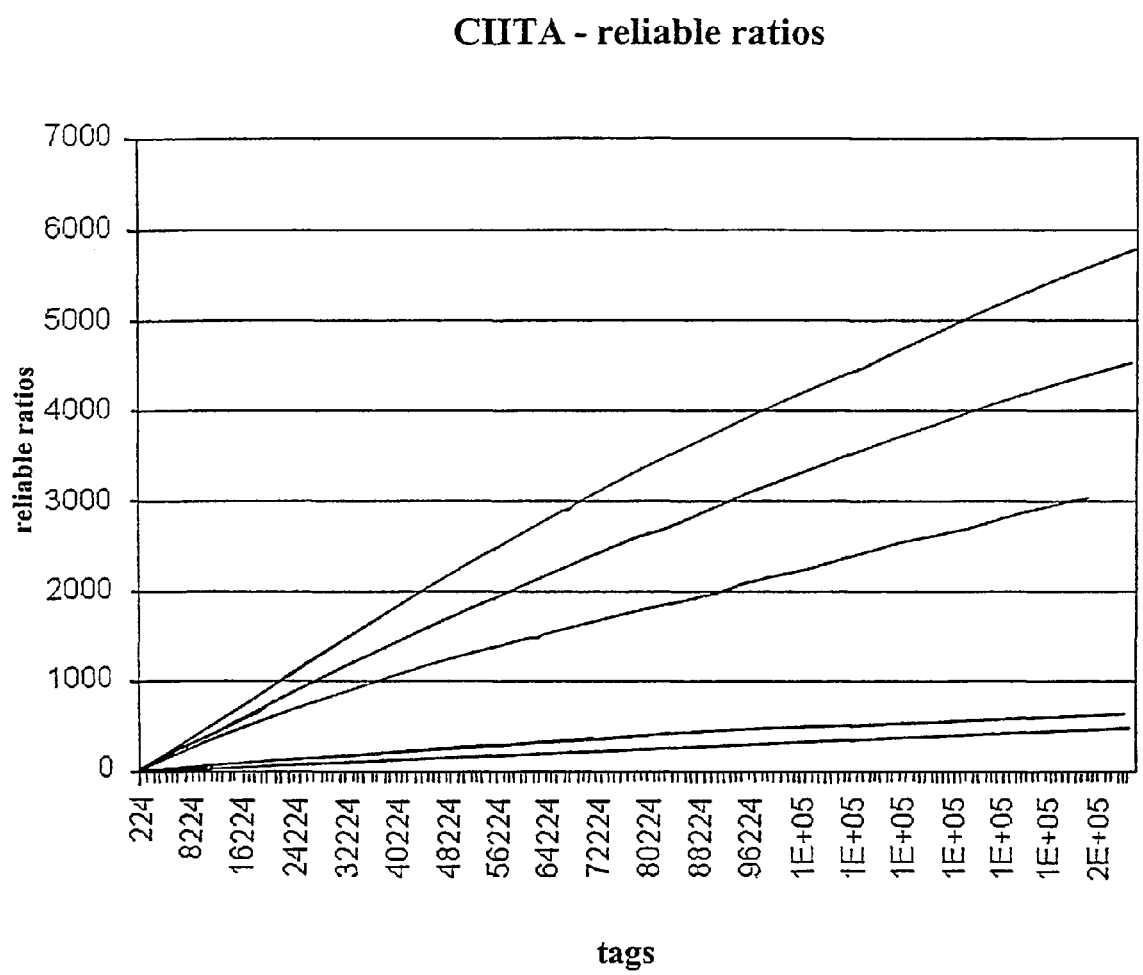

FIG. 16 shows for this example a graph of the type already discussed with reference to FIG. 4B.

Figure 17:
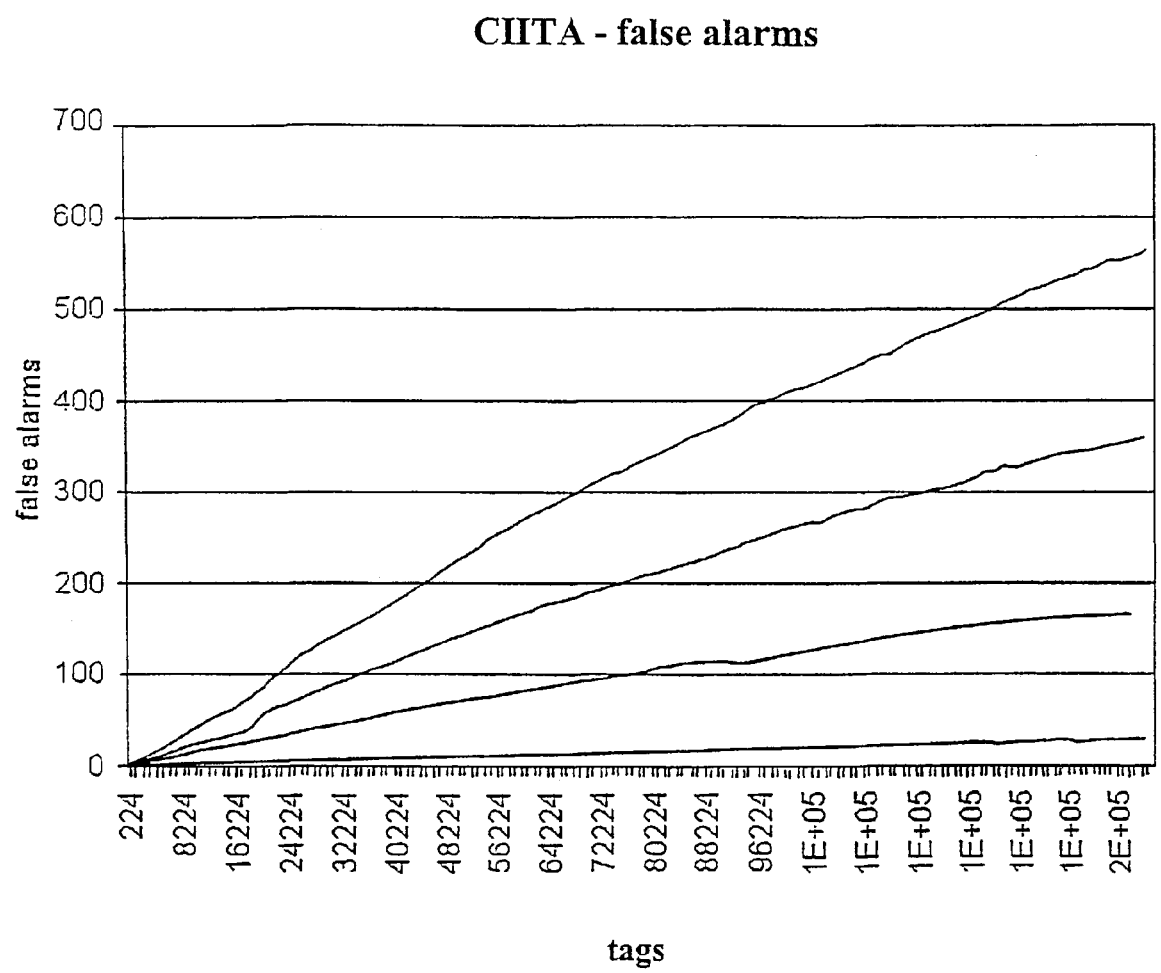

FIG. 17 shows for this example a graph relating to false alarms; and

FIG. 18 shows an extract from the list of the most regulated genes for this example.

Annexes 1 through 8 are enclosed to the present description and relate to exemplary program codes for performing the method according to the present invention.

Annexes 1 through 3 relate to the ditag and tag processing and contain the procedures SageprocessExt.pl, Ubgene6.c and SagecompareExt.pl. respectively.

Annexes 4 to 6 relate to an ad hoc database construction with reference to the EMBL case, and contain a procedure MakeDBIndex.pl (Annex 4) which gets the entries referenced by at least one SWISS-PROT entry, a procedure ExtractData.pl (Annex 5) and a procedure IdentifyRna.pl (Annex 6) which uses the ad hoc library to identify the tags.

Annexes 7 and 8 relate to the interface and contain procedures Displist.pl which creates the html page displaying data according to the selection criteria and SageChip-.java which represents a graphic interface applet.

The present invention has been up to now disclosed with reference to preferred embodiments. Other embodiments will be however apparent to the person skilled in the art, upon reading of the present description.

For example, tags with different numbers of base-pairs could be treated with easy changes to what up to now described.

It is also to be understood that other features can be added to the Graphic Web Interface in order to improve the accessibility to the tags data and to the KEGG pathways, without departing from the scope of the present invention.

The invention claimed is:

1. A method for identification of gene transcripts comprising the steps of:
    a) generating at least a first set of raw sequences by sequencing at least a first type of biological material;
    b) isolating first ditags from said at least first set of raw sequences;
    c) isolating first tags from said isolated at least first ditags;
    d) determining abundance of said first tags; and
    e) identifying said first tags, further comprising a step of
    f) rejecting said isolated first tags that are wrongly sequenced by means of a statistical model for sequencing errors to be applied to said isolated first tags, said statistical model being defined by a probability function F(a,b), wherein said function F is intended to modelize the probability that a given tag a can be sequenced as b.

2. The method of claim 1, wherein said statistical model of said step f) uses a confidence level of a base-calling method that has been converted into a probability that a base-pair is not correct.

3. The method of claim 1 or 2, wherein said step f) is applied after a step of
    g) rejecting said isolated first tags that are wrongly sequenced by checking correctness of said isolated first ditags or tags through a base-calling method.

4. The method of claim 2, wherein said base-calling method is performed through a base-calling software.

5. The method according to claim 1, wherein said ditags are isolated from said set of raw sequences through a method for serial analysis of gene expression (SAGE).

6. The method according to claim 3, wherein said steps a) through f) or a) through g) are applied to at least a second set of raw sequences and to respective second ditags and second tags, and further comprising a step of
    h) comparing said first tags and said second tags in order to determine relative abundance thereof.

7. The method according to claim 1, further comprising a step of predicting an extra base-pair for said tags.

8. The method of claim 7, wherein said step of predicting an extra base-pair for said tags comprises the steps of:
    assigning an extra base-pair to each tag of a ditag each time a ditag of at least a predetermined number of base-pairs is isolated;
    imposing for each of the tags to which an extra base-pair has been assigned to be as much abundant as a predetermined threshold;
    choosing, for each of the remaining tags, its most dominant extra base-pair; and
    imposing, for said most dominant extra base-pair, to represent at least a certain percentage of the number of occurrences of said tag.

9. The method according to claim 1, further comprising a step of checking correctness of said isolated ditags by determining the length of said ditags and rejecting ditags smaller and/or larger than a predetermined length.

10. The method according to claim 1, further comprising a step of checking correctness of said isolated ditags by determining an occurrence of said ditags and rejecting ditags occurring twice.

11. The method according to claim 1, wherein said statistical model of said step f) modelizes the probability that a given tag a can be sequenced as b by applying an average sequencing error rate to said function F(a,b).

12. The method of claim 11, wherein said average sequencing error rate is calculated through the system $$\begin{cases} k_n = d - (1 - (1-q)^n)N \\ k_m = d - (1 - (1-q)^m)N \end{cases}$$

wherein q represents said average sequencing error rate.

13. The method according to claim 1, wherein said step f) comprises a step of:
    f1) calculating an estimate of the abundance of said isolated first tags not rejected by means of said statistical model.

14. The method according to claim 13, wherein said step f1) is performed through a sparse diagonal-dominant linear system.

15. The method according to either one of claims 13 or 14, wherein said step f) further comprises the steps of:
    f2) calculating a difference between said estimate of the abundance of the tags and a counted abundance of the tags; and
    f3) eliminating tags for which said difference is bigger than a given threshold.

16. The method according to claim 6, wherein said step h) of comparing said first and at least second ditags in order to determine relative abundance thereof comprises the steps of:
    h1) merging said first and second tags;
    h2) normalizing the abundance of said first and second tags;
    h3) determining a difference of abundance between said first and second ditags; and
    h4) estimating correctness of said difference.

17. The method of claim 16, wherein said step h4) of estimating correctness of said difference applies a Claverie method.

18. The method according to claim 16, wherein said step h) of comparing said first and second ditags in order to determine relative abundance thereof further comprises the step of:
    h5) checking consistence of the predicted extra base-pair.

19. The method according to claim 6, wherein said step e) of identifying said at least first tags comprises the step of:
    e1) performing a first identification of the tags by comparison with a first database.

20. The method of claim 19, wherein said step e) of identifying said at least first tags further comprises the step of:
    e2) assigning a score to each of the tags identified by said first identification.

21. The method of claim 19, wherein said step e) of identifying said first and second tags further comprises the steps of:
    e3) performing at least a second identification of the tags by comparison with at least a second database; and
    e4) assigning a score to each of the tags identified by said at least second identification.

22. The method of claim 19, wherein said first database is an EST database.

23. The method of claim 22, wherein the step b) is performed by using MmeI as a restriction enzyme.

24. The method according to claim 1, further comprising a step of visualizing the identified tags.

25. The method of claim 24, further comprising a step of providing means for accessing the information concerning said identified tags.

26. The method of claim 24, further comprising a step for assigning a unique number for each identified tag.

27. The method according to claim 24, further comprising a step for assigning a unique position on a screen for each identified tag.

28. The method of claim 11, wherein said average sequencing error rate equals 1%.

29. The method according to claim 28, wherein, for every tag $a \in S_T$, $S_T$ being the set of every possible tag to be considered, the value of $F(a,b)$, $\in$ be $S_T$, is:

$$F(a, a) = C_{10}^{0}(0,01)^{0}(0,99)^{10} = (0,99)^{10}$$

i) if b = a, ii) if b≠a and (a) $V_a \subset S_T$ being the set of every "neighbour" tag $b \in S_T$ which can be "reached" from a by either base exchange, insertion and/or suppression (b) $N_a = \#V_a$, being the number of elements in the set $V_a$, $$F(a, b) = \frac{1 - (0,99)^{10}}{N_a}, \forall b \in V_a$$

$$F(a,b) = 0, \forall b \notin V_a.$$

* * * * *